United States Patent
Chaudhuri et al.

(10) Patent No.: US 7,144,870 B2
(45) Date of Patent: Dec. 5, 2006

(54) HYALURONIC ACID MEDIATED ADENOVIRAL TRANSDUCTION

(75) Inventors: Saumya-Ray Chaudhuri, West Bengal (IN); Mary Y. Hurwitz, Houston, TX (US); Vien Holcombe, Houston, TX (US); Karen T. Marcus, Sugarland, TX (US); Richard L. Hurwitz, Houston, TX (US)

(73) Assignee: Research Development Foundation, Carson City, NV (US)

( * ) Notice: Subject to any disclaimer, the term of this patent is extended or adjusted under 35 U.S.C. 154(b) by 538 days.

(21) Appl. No.: 10/367,581

(22) Filed: Feb. 14, 2003

(65) Prior Publication Data

US 2003/0186936 A1 Oct. 2, 2003

Related U.S. Application Data

(60) Provisional application No. 60/357,485, filed on Feb. 15, 2002.

(51) Int. Cl.
C07H 21/04 (2006.01)
C12N 15/63 (2006.01)
C12N 5/00 (2006.01)

(52) U.S. Cl. ............... 514/44; 536/23.1; 435/320.1; 435/325

(58) Field of Classification Search .............. 514/44
See application file for complete search history.

(56) References Cited

U.S. PATENT DOCUMENTS

| | | | |
|---|---|---|---|
| 4,141,973 A | 2/1979 | Balazs | 514/54 |
| 4,801,619 A | 1/1989 | Lindblad | 514/825 |
| 4,808,526 A | 2/1989 | Lawford | 435/161 |
| 4,840,941 A | 6/1989 | Ueno et al. | 514/59 |
| 5,670,488 A | 9/1997 | Gregory et al. | 514/44 |
| 5,824,544 A | 10/1998 | Armentano et al. | 435/320.1 |
| 5,932,210 A | 8/1999 | Gregory et al. | 424/93.2 |
| 6,194,392 B1 | 2/2001 | Falk et al. | 514/54 |
| 6,218,373 B1 | 4/2001 | Falk et al. | 514/54 |
| 6,258,791 B1 | 7/2001 | Braun | 514/44 |
| 6,271,216 B1 | 8/2001 | Mello et al. | 424/678 |
| 6,312,681 B1 | 11/2001 | Engler et al. | 424/93.2 |
| 2001/0046965 A1 | 11/2001 | Ayares et al. | 514/44 |
| 2002/0004040 A1 | 1/2002 | Kovesdi et al. | 424/93.21 |

FOREIGN PATENT DOCUMENTS

| CA | 2131130 | 3/1996 |
|---|---|---|
| WO | WO 97/15330 | 5/1997 |

OTHER PUBLICATIONS

Gunther, M et al. Curr Med Chem Anti-Cancer Agents 5(2):157-71, 2005.*

Chevez-Barrios et al., "Gene therapy for retinoblastoma: comparison of gene repalcement with RB gene suicide gene," *Laboratory Investigation*, 80(3):198A, #1167, 2000.

Abe et al., "Transduction of a drug-sensitive toxic gene into human leukemia cell lines with a novel retroviral vector (43611)," *Proc. Soc. Exp. Biol. Med.*, 203:354-359, 1993.

Banerjee et al. "Changes in growth and tumorigenicity following reconstitution of retinoblastoma gene function in various human cancer cell types by microcell transfer of chromosome 13[1]," *Cancer Res.*, 52:6297-6304, 1992.

Behbakht et al., "Adenovirus-mediated gene therapy of ovarian cancer in a mouse model," *Am. J. Obstet. Gynecol.*, 175(5):1260-1265, 1996.

Bett et al., Packaging capacity and stability of human adenvirus type 5 vectors, *J. Virol.*, 67(10):5911-5921, 1993.

Blackwell et al., "Retargeting to EGFR enhances adenovirus infection efficiency of squamous cell carcinoma," *Arch. Otolaryngol. Head. Neck Surg.*, 125(8):856-863, 1999.

Chen et al., "Combination gene therapy for liver metastasis of colon carcinoma in vivo," *Proc. Natl. Acad. Sci. USA*, 92(7):2577-2581, 1995.

Chen et al., "Gene therapy for brain tumors: regression of experimental gliomas by adenovirus-mediated gene transfer in vivo," *Proc. Natl. Acad. Sci. USA*, 91(8):3054-3057, 1994.

Chillon et al., "Group D adenovirous infect primary central nervous system cells more efficiently than those from group C," *J. Virol.*, 73(3):2537-2540, 1999.

Chroboczek et al., "The sequence of the genome of adenovirus type 5 and its comparison with the genome of adenovirus type 2," *Virology*, 186:280-285, 1992.

da Cruz et al., "Dynamics of gene transfer to retinal pigment epithelium," *Invest. Opthalmol. Vis. Sci.*, 37(12):2447-2454, 1996.

Dorai et al., "A recombinant defective adenoviral agent expressing anti-Bcl-2 ribozyme promotes apoptosis of Bcl-2-expressing human prostate cancer cells," *Int. J. Cancer*, 82(6):846-852, 1999.

Eastham et al., "Prostate cancer gene therapy: herpes simplex virus thymidine kinase gene transduction followed by ganciclovir in mouse and human prostate cancer models," *Hum. Gene Ther.*, 7(4):515-523, 1996.

Esandi et al., "Gene therapy of experimental malignant mesothelioma using adenovirous vectors encoding the HSVtk gene," *Gene Ther.*, 4(4):280-287, 1997.

Evans, "Latent adenovirus infections of the human respiratory tract," *Am. J. Hyg.* 67:256-263, 1958.

Feldman et al., "Perspectives of arterial gene therapy for the prevention of restenosis," *Cardiovasc. Res.*, 32(2):194-207, 1996.

Flomenberg et al., "Increasing incidence of adenovirus disease in bone marrow transplant recipients," *J. Infect. Dis.*, 169:775-781, 1994.

Goebel et al., "Adenovirus-mediated gene therapy for head and neck squamous cell carcinomas," *Ann. Otol. Rhinol. Laryngol.*, 105(7):562-567, 1996.

(Continued)

*Primary Examiner*—Joseph Woitach
*Assistant Examiner*—Marcia S. Noble
(74) *Attorney, Agent, or Firm*—Fulbright and Jaworski L.L.P.

(57) ABSTRACT

The present invention provides methods of treatment of adenoviral mediated disease, improved methods for transducing cells with adenoviral and related vectors, and improved methods of gene therapy utilizing such methods.

12 Claims, 15 Drawing Sheets

OTHER PUBLICATIONS

Goldstein et al, "Defective lipoprotein receptors and atherosclerosis-lessons from an animal counterpart of familial hypercholesterolemia," *New Engl. J. Med.*, 309(11983):288-296, 1983.

Graham and Prevec, "Methods for construction of adenovirus vectors," *Mol Biotechnol.*, 3(3):207-220, 1995.

Han et al., "Receptor-mediated gene transfer to cells of hepatic origin by galactosylated albumin-polylysine complexes," *Biol. Pharm. Bull.*, 22(8):836-840, 1999.

Hermens and Verhaagen, "Viral vectors, tools for gene transfer in the nervous system," *Prog. Neurobiol.*, 55(4):399-432, 1998.

Hoekstra, "Hyaluronan-modified surfaces for medical devices," *Medical Device & Diagnostic Industry Magazine*, Feb. 1999.

Horwitz, In: *Virology*, 2d edit., Fields (Ed.), Raven Press, Ltd. New York, 1990.

Hurwitz et al., "Suicide gene therapy for treatment of retinoblastoma in a murine model," *Hum. Gene Ther.*, 10:441-448, 1999.

Irie et al., "Therapeutic efficacy of an adenovirus-mediated anti-H-ras ribozyme in experimental bladder cancer," *Antisense Nucleic Acid Drug Dev.*, 9(4):341-349, 1999.

Ishibashi et al, "Hypercholesterolemia in low density lipoprotein receptor knockout mice and its reversal by adenovirus-mediated gene delivery," *J. Clin. Invest.*, 92:883-893, 1993.

Ishibashi et al, "Massive xanthomatosis and atherosclerosis in cholesterol-fed low density lipoprotein receptor-negative mice," *J. Clin. Invest.*, 93:1885-1893, 1994.

Kreil, "Hyalurnidases—a group of neglected enzymes," *Protein Sci.*, 4(9):1666-1669, 1995.

Laurent et al., (eds.) *The Chemistry, Biology and Medical Applications of Hyaluronan and its Derivatives*, Wenner-Gren International Series, vol. 72, c1998.

Lee and Spicer, "Hyaluronan: a multifunctional, megaDalton, stealth molecule," *Curr. Opin. Cell Biol.*, 12:581-586, 2000.

Lesch, "Gene transfer to the brain: emerging therapeutic strategy in psychiatry?" *Biol Psychiatry*, 45(3):247-253, 1999.

Marienfeld et al., "Autoreplication of the vector genome in recombinant adenoviral vectors with different E1 region deletions and transgenes," *Gene Ther.*, 6(6):1101-1113, 1999.

Mincheff et al., "Naked DNA and adenoviral immunizations for immunotherapy of prostate cancer: a phase I/II clinical trial," *Eur. Urol.*, 38(2):208-217, 2000.

Morrison et al., "Complete DNA sequence of canine adenovirous type 1," *J. Gen. Virol.*, 78(Pt 4):873-878, 1997.

Neumann et al., "Detection of adenovirus nucleic acid sequence in human tonsils in the absence of infectious virus," *Virus Res.*, 7:93-97, 1987.

O'Malley et al., "Adenovirus-mediated gene therapy for human head and neck squamous cell cancer in a nude mouse model," *Cancer Res.*, 55(5):1080-1085, 1995.

Parks et al., "A helper-dependent system for adenovirus vector production helps define a lower limit for efficient DNA packaging," *J. Virol.*, 71(4):3293-3298, 1997.

Petrof, "Respiratory muscles as a target for adenovirus-mediated gene therapy," *Eur. Respir. J.*, 11(2):492-497, 1998.

Reddy et al., "Nucleotide sequence and transcription map of procine adenovirus type 3," *Virology*, 251(2):414-426, 1998.

Robbins et al., "Viral vectors for gene therapy," *Trends Biotechnol.*, 16(1):35-40, 1998.

Rooney et al., "Use of gene-modified virus-specific T lymphocytes to control Epstein-Barr-virus-related lymphoproliferation," *Lancet.*, 345:9-13, 1995.

Rosenfeld et al., "Adenoviral-mediated delivery of herpes simplex virus thymideine kinase results in tumor reduction and prolonged survival in a SCID mouse model of human ovarian carcinoma," *J. Mol. Med.*, 74(8):455-462, 1996.

Schmitz et al., "Worldwide epidemiology of human adenovirus infections," *Am. J. Epidemiol.*, 117-455-466, 1983.

Shiver et al., "Replication-incompetent adenoviral vaccine vector elicits effective anti-immunodeficiency-virus immunity," *Nature*, 415:331-335, 2002.

SIGMA™ 2002-2003 Catalog of Biochemical and Reagents for Life Science research. Sigma-Aldrich Co., Inc. P.O. Box 14508, St. Louis, MO 63178, USA, 2002.

Spandidos et al., "Expression of the normal H-ras1 gene can suppress the transformed and tumorigenic phenotypes induced by mutant ras genes," *Anticancer Res.*, 10:1543-1554, 1990.

Spicer and McDonald, "Characterization and molecular evolution of a vertebrate hyaluronan synthase gene family," *J. Biol. Chem.*, 273:1923-1932, 1998.

Spicer, "In vitro assays for hyaluronan synthase," *Methods Mol. Biol.*, 171:373-382, 2001.

Stewart et al., "Adenovector-mediated gene delivery of interleukin-2 in metastatic breast cancer and melanoma: results of a phase 1 clinical trial," *Gene Ther.*, 6(3):350-363, 1999.

Tanzawa et al., "WHHL-rabbit: a low density lipoprotein receptor-deficient animal model for familial hypercholesterolemia," *FEBS Letters*, 118(1):81-84, 1980.

Vanderkwaak and Alvarez, "Immune directed therapy for ovarian carcinoma," *Curr. Opin. Obstet. Gynecol.*, 11(1):29-34, 1999.

Wadell et al., "Genetic variability of adenoviruses," *Ann. NY Acad. Sci.*, 354:16-42, 1980.

Watanabe, "Serial inbreeding of rabbits with hereditary hyperlipidemia (WHHL-rabbit)," *Atherosclerosis*, 36:261-268, 1980.

Wilson, "Vehicles for gene therapy," *Nature*, 365:691-692, 1993.

Wilson, "When bad gene transfer if good," *J. Clin. Invest.*, 98(11):2435, 1996.

Yotnda et al., "Efficient infection of primitive hematopoietic stern cells by modified adenovirus," *Gene Ther.*, 8:930-937, 2001.

Chevez-Barrios et al., "Response to retinoblastoma with vitreous tumor seeding to adenovirus-mediated delivery of thymidine kinase followed by ganciclovir," *J. of Clinical Oncology*, 23:7927-7935, 2005.

Mallam et al., "Efficient gene transfer into retinal cells using adenoviral vectors: dependence on receptor expression," *Investigative Ophthalmology & Visual Science*, 45:1680-1687, 2004.

Shayakhmetov et al., "Efficient gene transfer into human cd34+ cells by a retargeted adenovirus vector," *J of Virology.* 74:2567-2583, 2000.

Bourguignon et al., "Interaction between the adhesion receptor, CD44, and the oncogene product, p 185HER2, promotes human ovarian tumor cell activation," *Bio. Chem.*, 272:27913-27918, 1997.

* cited by examiner

Vitreous Enhances Adenoviral-mediated Transgene Expression in Cells Transduced Using an Alternate Adenoviral Receptor

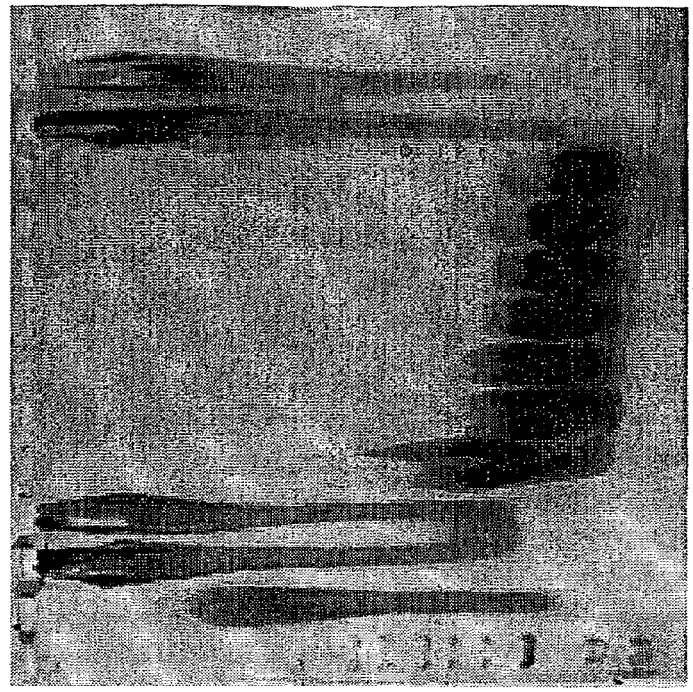

Lyase Digestion of High Molecular Weight (HMW) Hyaluron

- Lane 1: 1 kb DNA Ladder
- Lane 2: Rooster Comb Hyaluron (LMW)
- Lane 3: Undigested Hyaluron (HMW)
- Lane 4: Hyaluron + Boiled Lyase t0
- Lane 5: Hyaluron + 0.1 mg Lyase t0
- Lane 6: Hyaluron + 0.1 mg Lyase t5'
- Lane 7: Hyaluron + 0.1 mg Lyase t10'
- Lane 8: Hyaluron + 0.1 mg Lyase t15'
- Lane 9: Hyaluron + 0.1 mg Lyase t20'
- Lane 10: Hyaluron + 0.1 mg Lyase t30'
- Lane 11: Hyaluron + 0.1 mg Lyase t60'
- Lane 12: Hyaluron + Boiled Lyase t60'
- Lane 13: "Old" Hyaluron
- Lane 14: Blank

FIG. 14 sual Application Ser. No. 60/357,485 filed Feb. 15, 2002,
HYALURONIC ACID MEDIATED ADENOVIRAL TRANSDUCTION

BACKGROUND OF THE INVENTION

The present application claims the benefit of U.S. Provisional Application Ser. No. 60/357,485 filed Feb. 15, 2002, the entire text of which is herein incorporated by reference.

1. Field of the Invention

The present invention is directed to the fields of molecular biology, gene therapy, and treatment of viral disease. More specifically, the present invention relates to methods of treatment of adenoviral infection and disease, to improved methods for expressing transgenes introduced into cells with adenoviral and related vectors, and improved methods of gene therapy utilizing such methods.

2. Description of Related Art

Wild-type adenoviruses are associated with a variety of human diseases including respiratory, ocular, and gastrointestinal infections. These infections are a major cause of school absenteeism for children and of loss of work productivity for adults. In immuno-compromised individuals, infection with adenovirus currently has no effective antiviral treatment and is frequently fatal. Adenovirus infections may thus be lethal to immunocompromised patients who have received chemotherapy, bone marrow transplants, other organ transplants, or suffer from AIDS. Pediatric bone marrow transplant patients are particularly susceptible, with 10–30% developing adenovirus infection.

There are no anti-viral compounds that are effective against adenovirus infections. Thus, there is a need in the art to develop an effective treatment for adenoviral infection, especially for immunocompromised individuals.

In contrast, non-pathogenic replication-defective adenoviral vectors are useful for many preclinical and clinical gene therapy applications. Human gene therapy is an approach to treating human disease that is based on the modification of gene expression in cells of the patient. It has become apparent over the last decade that the single most outstanding barrier to the success of gene therapy as a strategy for treating inherited diseases, cancer, and other genetic dysfunctions is the development of useful gene transfer and expression vehicles. Eukaryotic viruses have been employed as vehicles for somatic gene therapy. Among the viral vectors that have been cited frequently in gene therapy research are adenoviruses.

Modified adenoviruses that are replication incompetent and therefore non-pathogenic are being used as vehicles to deliver therapeutic genes for a number of metabolic and oncologic disorders. These adenoviral vectors may be particularly suitable for disorders such as cancer that would best be treated by transient therapeutic gene expression since the DNA is not integrated into the host genome and the transgene expression is limited. Adenoviral vector may also be of significant benefit in gene replacement therapies, wherein a genetic or metabolic defect or deficiency is remedied by providing for expression of a replacement gene encoding a product that remedies the defect or deficiency.

Adenoviruses can be modified to efficiently deliver a therapeutic or reporter transgene to a variety of cell types. Recombinant adenoviruses types 2 and 5 (Ad2 and AdV5, respectively), which cause respiratory disease in humans, are among those currently being developed for gene therapy. Both Ad2 and AdV5 belong to a subclass of adenovirus that are not associated with human malignancies. Recently, the hybrid adenoviral vector AdV5/F35 has been developed and proven of great interest in gene therapies and related studies (Yotnda et al., 2001).

Recombinant adenoviruses are capable of providing extremely high levels of transgene delivery. The efficacy of this system in delivering a therapeutic transgene in vivo that complements a genetic imbalance has been demonstrated in animal models of various disorders (Watanabe, 1986; Tanzawa et al., 1980; Golasten et al., 1983; Ishibashi et al., 1993; and S. Ishibashi et al., 1994). Indeed, a recombinant replication defective adenovirus encoding a cDNA for the cystic fibrosis transmembrane regulator (CFTR) has been approved for use in at least two human CF clinical trials (Wilson, 1993). Hurwitz, et al., (1999) have shown the therapeutic effectiveness of adenoviral mediated gene therapy in a murine model of cancer (retinoblastoma).

Unfortunately, adenoviral vectors, although effective at transducing target cells, do not necessarily result in the desired level of expression of the transgene in the target cells and tissues. An exception has been noted in the ocular environment where relatively high levels of transgene expression have been observed.

There is therefore a need for effective treatment of wild type adenoviral infection, especially in immunocompromised individuals. There is also a need for methods and compositions that are effective in enhancing the expression of transgenes introduced into a wide variety of cell types and tissue.

SUMMARY OF THE INVENTION

The present invention is directed to compositions and methods useful in the treatment of adenoviral mediated disease and adenoviral infection and improved expression of transgenes delivered to cells using adenoviral and related vectors.

Therefore, a preferred embodiment of the present invention is a method of treating adenoviral disease comprising identifying a subject in need of treatment for adenoviral disease and administering to the subject a composition comprising an adenoviral inhibitor in an amount sufficient to inhibit or prevent adenoviral disease. Another preferred embodiment is a method for inhibiting adenovirus infection comprising administering to a cell a composition comprising an adenovirus inhibitor in an amount sufficient to inhibit the progress of adenovirus infection.

A related embodiment is a method for treating adenoviral disease comprising identifying a subject in need of treatment for adenoviral infection and inhibiting adenoviral infection by administering to a cell of the subject a composition comprising an adenovirus inhibitor in an amount sufficient to inhibit the progress of adenovirus infection. An additional preferred embodiment is a method for treating adenoviral disease comprising identifying a subject in need of treatment and administering to adenoviral or adenoviral vector transduces cells of the subject an inhibitor of adenoviral-mediated transgene expression.

A further preferred embodiment is a method of inhibiting transgene expression comprising obtaining a cell transduced with an adenovirus or adenoviral vector and contacting the cell with an inhibitor of adenoviral-mediated transgene expression. In further preferred aspects, the cell is part of a tissue. Additional preferred embodiments include those wherein the cell is a vertebrate cell, a mammalian cell, a primate cell, or a human cell. Of course, the cell may be non-human. In particular embodiments, the subject of treatment is human. In others, the subject of treatment is non-human.

In certain preferred embodiments, the adenoviral inhibitor comprises low molecular weight hyaluron. The molecular weight of low molecular weight hyaluron is contemplated to be such that the hyaluron has an average molecular weight that may range from less than 750,000 Da to the lowest molecular weights of hyaluronic acid, i.e. a single repeating unit. Therefore, it is contemplated that the average molecular weight of low molecular weight hyaluron may be less than 750,000; 650,000; 600,000; 550,000; 500,000; 450,000; 400,000; 350,000; 300,000; 250,000; 200,000; 150,000; 100,000; 50,000 Da or less or any range derivable therein.

An alternative means of denoting low molecular weight hyaluron within embodiments of the present invention is where the low molecular weight hyaluron displays a substantially lower molecular weight than high molecular weight hyaluron. In particular embodiments the low molecular weight hyaluron displays a substantially lower molecular weight than high molecular weight hyaluron when compared by agarose gel electrophoresis.

In additional embodiments of the invention, the adenoviral inhibitor comprises degradation products of high molecular weight hyaluron. Such degradation products may be obtained by a number of means. In one embodiment, the degradation products are comprised of out of date hyaluron. Out of date hyaluron is defined as hyaluron that is past the date beyond which the hyaluron would not be acceptable as a clinical composition or as useful as high molecular weight hyaluron. Such dates are typically provided on commercial samples of hyaluron by the manufacturer but may also be determined by routine experimentation. Similarly, in another embodiment, the inhibitor comprises degradation products of vitreous. In one such embodiment, such degradation products are out of date vitreous.

In further embodiments the adenoviral inhibitor comprises the products of treatment of high molecular weight hyaluron with lyase or hyaluronidase. Similarly, in one embodiment the inhibitor comprises vitreous treated with lyase or hyaluronidase.

In further preferred embodiments cells to be treated are incubated in a solution comprising the inhibitor. In specific embodiments thereof, the inhibitor is low molecular weight hyaluron. The concentration of the low molecular weight hyaluron may range from about 30 micrograms per 100 microliters of solution to more than 240 micrograms per 100 microliters. Thus, the concentration of low molecular weight hyaluron may be 30 micrograms per 100 microliters, 60 micrograms per 100 microliters, 120 micrograms per 100 microliters, or 240 micrograms per 100 microliters or any concentration derivable therein. Further, in particular embodiments, the concentration of low molecular weight hyaluron may approach saturation.

Because the scope of the invention includes methods and compositions for the enhancement of adenoviral-mediated transgene expression, a preferred embodiment is a method for enhancing transgene expression in a cell comprising obtaining a cell transduced by an adenoviral vector and contacting the cell with an enhancer of adenoviral-mediated transgene expression.

In certain embodiments the cell may be contacted with the enhancer over a time period of from 2 to 20 hours after transduction, or any range derivable therein. Preferred embodiments include those wherein the cell is contacted with the enhancer over a time of from 2 to 4, 6, or 8 hours after transduction, or any shorter time period within those. In certain embodiments the cell is contacted with the enhancer 2 hours after transduction. Of course, in certain other preferred embodiments, the cell is contacted with the enhancer substantially simultaneously with transduction. In yet further preferred embodiments, the cell is contacted with the enhancer continuously from transduction onwards.

In preferred embodiments of the invention relating to enhancement of adenoviral-mediated transgene expression the enhancer comprises vitreous, high molecular weight hyaluron, or mixtures thereof. In particular embodiments the enhancer comprises low molecular weight hyaluron in combination with vitreous. In further particular embodiments the enhancer is vitreous. In other certain preferred embodiments the enhancer is high molecular weight hyaluron.

Preferred related embodiments comprise the step of incubating a cell transduced by an adenovirus or adenoviral vector in a composition comprising the enhancer. When the enhancer is vitreous, particular embodiments include those wherein the concentration of vitreous in the composition is in the range of 0.5% to 5% (v/v). Specific embodiments include those wherein the concentration of vitreous in the composition is about 0.5%, 2.5%, or 5%.

In yet further preferred embodiments the enhancer comprises high molecular weight hyaluron. The molecular weight of high molecular weight hyaluron is contemplated to be such that the hyaluron has an average molecular weight that may range from more than 750,000 Da to the highest molecular weights of hyaluron, i.e. over several million Da or more. Therefore, it is contemplated that the average molecular weight of high molecular weight hyaluron may be greater than 650,000; 750,000; 1,000,000; or more, or any range derivable therein.

An alternative means of denoting high molecular weight hyaluron within embodiments of the present invention is where the high molecular weight hyaluron displays a substantially higher molecular weight than low molecular weight hyaluron. In particular embodiments the high molecular weight hyaluron displays a substantially higher molecular weight than low molecular weight hyaluron when compared by agarose gel electrophoresis.

When the enhancer is high molecular weight hyaluron, certain embodiments comprise concentrations of high molecular weight hyaluron ranging from 10 micrograms per 100 microliters to more than 100 micrograms per 100 microliters in a composition in which a cell is incubated.

Embodiments of the invention are not limited by the specific adenovirus or adenoviral vector employed. The inventors have discovered a means of enhancing or inhibiting adenoviral infection and transgene expression that is general to adenovirus and vectors derived therefrom. Of course, in specific embodiments the enhancer is contacted to a cell that is infected by adenovirus. In other particular embodiments, it is contemplated that the adenoviral vector be derived from adenovirus 5 or adenovirus 2 and their relatives. Of course, when formulated into a vector, adenoviral constructs may comprise transgenes for expression within cells.

Particular transgenes whose expression are contemplated for enhancement or inhibition by the methods and compositions of the present invention include, but are not limited to transgenes useful in treating cancer. In preferred embodiments the transgene is a gene useful in the treatment of retinoblastoma. In further particular embodiments the transgene is a retinoblastoma (RB) gene or a thymidine kinase (TK) gene. In other embodiments the transgene is a tumor suppressor gene. In particular embodiments, the tumor suppressor gene encodes p53. In other preferred embodiments, the transgene encodes a reporter gene. Reporter genes are well known to those of skill in the art and the choice of reporter gene is not limiting to the invention. Embodiments include those wherein the transgene is a luciferase, a green fluorescent protein, or a Beta-galactosidase gene.

The invention provides for enhancement of adenoviral-mediated transgene expression in cells. In particular embodiments the cell is part of a tissue. In further embodiments the cell is a vertebrate cell, a mammalian cell, a primate cell, or a human cell.

The inventors have additionally discovered a role for the CD44 protein in modulating transgene expression in the presence of hyaluron or vitreous. Therefore, one embodiment is a method of modulating transgene expression comprising contacting a cell transfected with an adenoviral vector and with at least one antibody specific to CD44. Related embodiments include the step of contacting the cell with high molecular weight hyaluron or vitreous either before, during, or after contacting the cell with at least one antibody specific to CD44. In certain embodiments the antibodies include at least one monoclonal antibody. In additional embodiments the antibody is KM114.

Further embodiments of the invention include a kit for the production of enhanced transgene expression comprising high molecular weight hyaluron or vitreous and components for adenoviral vector transfection.

Even further embodiments comprise methods of screening for forms of hyaluron. As will be appreciated by those of skill in the art, forms of hyaluron may be classified by their chemical structure, chemical properties, physical properties, and within the context of the invention, their effects upon adenoviral-mediated transgene expression. Non-limiting examples of such forms are high molecular weight hyaluron, low molecular weight hyaluron, hyaluron effective in inhibiting adenoviral-mediated transgene expression, and hyaluron effective in enhancing adenoviral-mediated transgene expression, and hyaluron effective in the treatment of adenoviral disease.

Therefore, certain embodiments comprise obtaining a first sample of hyaluron (a); obtaining a second sample of hyaluron of known form (b); and comparing the effects of the sample obtained in (a) on adenoviral-mediated transgene expression with the effects of the sample obtained in (b) on adenoviral-mediated transgene expression, wherein enhanced transgene expression indicates hyaluron of expression enhancing form and inhibited transgene expression indicates hyaluron of expression inhibiting form. Similarly, certain embodiments comprise the steps of comparing the samples of (a) and (b) by gel electrophoresis and correlating the electrophoretic mobility of the samples of (a) and (b) with their effects on adenoviral-mediated transgene expression. Particularly preferred embodiments comprise agarose gel electrophoresis.

Following long-standing patent law, the words "a" and "an," when used in conjunction with the word "comprising" in the claims or specification, denotes one or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 14. Lyase Digestion of High Molecular Weight (HMW) Hyaluron.

DETAILED DESCRIPTION OF THE INVENTION

Figure 1:
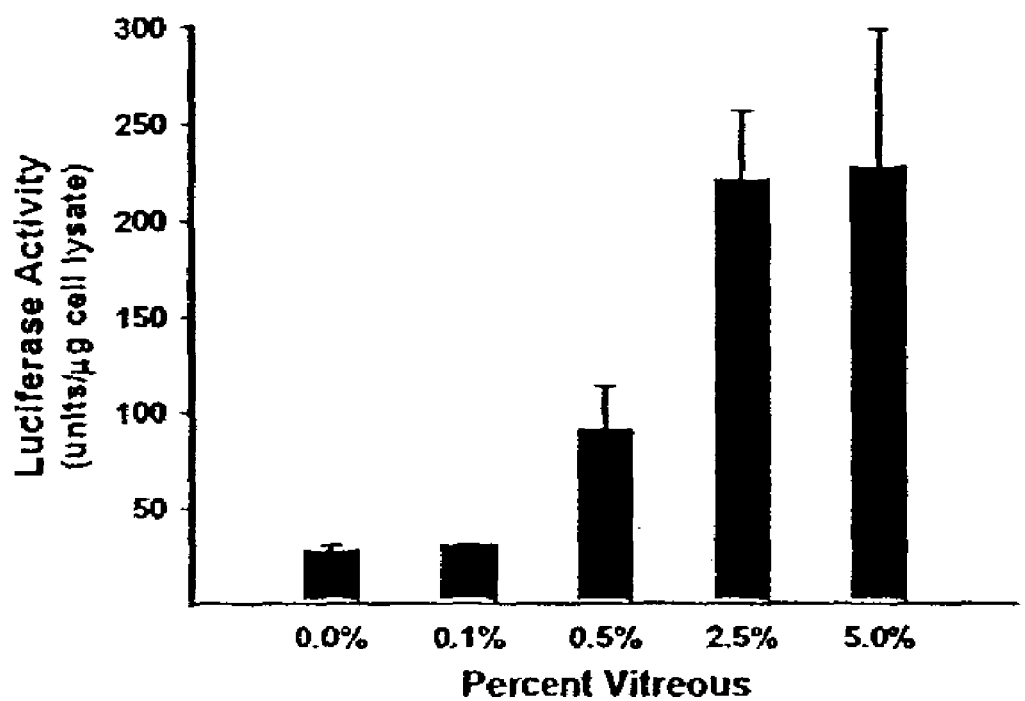
FIG. 1. Vitreous enhances adenoviral-mediated transgene expression. Bars represent standard error from the mean.

The inventors have made the surprising discovery that an important component of the vitreous of the eye, hyaluron, modulates the expression of transgenes introduced into cells by adenoviral vectors and infectivity of wild type adenovirus. Surprisingly, the inventors have discovered that high molecular weight hyaluron, either on its own or as a component of vitreous, acts to enhance the expression of functional transgenes introduced into cells by adenoviral vectors outside of the ocular environment both in vivo and in vitro. This enhancement of expression is independent of attachment and entry of the adenoviral vector into the cell.

Even more surprising and significant is the inventors' discovery that low molecular weight hyaluron acts to inhibit adenoviral infection and adenovector transduction. Most significantly, hyaluron of low molecular weight, or that which has been modified or degraded by enzymatic or other treatment may be used to treat adenoviral infection and disease. Thus, low molecular weight or modified hyaluron or vitreous may serve as a prophylactic or therapeutic composition for the treatment of adenoviral infection.

By acting to inhibit is meant that an agent acts to partially or completely hinder, restrain, slow, diminish, retard, reduce, suppress, repress or interfere with a biological process to any extent, partially or completely. Thus, an inhibitor is an agent that is capable of partially or completely hindering, restraining, slowing, diminishing, retarding, curbing, restraining, reducing, suppressing, repressing or interfering with a biological process such as a biochemical reaction, viral or cellular growth or other physiological process, including, but not limited to infection or disease processes, disease or life cycle progress, organ function or performance and the like.

The inventors have further discovered that hyaluron activates a series of intracellular events through its interaction with CD44, a member of a family of adhesion molecules commonly found on many cell types. Thus, an antibody that specifically binds to the hyaluron binding domain and blocks hyaluron activation of CD44 inhibits both vitreous-enhanced and base line adenoviral-mediated transgene expression. Jurkat cells that have been engineered to express CD44, but not wild-type Jurkat cells, which are known not to express CD44 or any other hyaluron-binding receptor, can be shown to exhibit enhanced transgene expression delivered by adenoviral vectors in the presence of vitreous or high molecular weight hyaluron. Phorbol ester greatly enhanced the effect caused by vitreous. Previous reports have shown that PMA causes oligomerization and activation of CD44. Low molecular weight hyaluron, which can be produced by incubation with lyase (or by using outdated or degraded hyaluron), not only failed to enhance adenoviral-mediated transgene expression but surprisingly and unexpectedly inhibited base-line adenoviral vector-mediated transgene expression.

The enhancement effect is independent of the promoter or the transgene used but is specific for adenoviral vectors even if they use different binding and internalization receptors. A time course of this effect suggests that hyaluron enhancement of adenoviral-mediated transgene expression occurs after viral binding and internalization.

Previous reports have demonstrated that high molecular weight hyaluron can bind and activate CD44 signal transduction but low molecular weight hyaluron can bind but not activate the same mechanism. Thus low molecular weight hyaluron serves as an inhibitor of CD44 function. High molecular weight hyaluron enhances adenoviral-mediated transgene expression while low molecular weight hyaluron inhibits base line adenoviral transduction. The glucuronic acid—N-acetyl glucosamine disaccharide that forms the base unit of hyaluron can activate CD44 but only when injected intracellularly. CD44 has been implicated in many cellular functions including serving as a cell trafficking protein, controlling cytoskeleton structure and motility, and regulating intracellular protein trafficking by controlling microtubule and actin assembly. A CD44 regulatory cascade mediated by low molecular weight G-proteins may affect many of these functions.

1. Adenoviruses

Adenoviruses comprise linear double stranded DNA, with a genome ranging from 30 to 35 kb in size (Reddy et al., 1998; Morrison et al., 1997; Chillon et al., 1999). There are over 50 serotypes of human adenovirus, and over 80 related forms which are divided into six families based on immunological, molecular, and functional criteria (Wadell et al, 1980). Physically, adenovirus is a medium-sized icosahedral virus containing a double-stranded, linear DNA genome which, for adenovirus type 5, is 35,935 base pairs (Chroboczek et al., 1992). Adenoviruses require entry into the host cell and transport of the viral genome to the nucleus for infection of the cell and replication of the virus.

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a y sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100–200 bp in length), are cis elements, function as origins of replication and are necessary for viral DNA replication. The $\psi$ sequence is required for the packaging of the adenoviral genome.

The mechanism of infection by adenoviruses, particularly adenovirus serotypes 2 and 5, has been extensively studied. A host cell surface protein designated CAR (Coxsackie Adenoviral Receptor) has been identified as the primary binding receptor for these adenoviruses. The endogenous cellular function of CAR has not yet been elucidated. Interaction between the fiber knob and CAR is sufficient for binding of the adenovirus to the cell surface. However, subsequent interactions between the penton base and additional cell surface proteins, members of the $\alpha_v$ integrin family, are necessary for efficient viral internalization. Disassembly of the adenovirus begins during internalization; the fiber proteins remain on the cell surface bound to CAR. The remainder of the adenovirus is dissembled in a stepwise manner as the viral particle is transported through the cytoplasm to a pore complex at the nuclear membrane. The viral DNA is extruded through the nuclear membrane into the nucleus where viral DNA is replicated, viral proteins are expressed, and new viral particles are assembled. Specific steps in this mechanism of adenoviral infection may be potential targets to modulate viral infection and gene expression.

2. Engineered Adenoviruses and Adenoviral Vectors

In particular embodiments, an adenovirus expression vector is contemplated for the delivery of expression constructs. "Adenovirus expression vector" or "Adenoviral vector" is meant to include those constructs containing adenovirus sequences sufficient to (a) support packaging of the construct and (b) to ultimately express a tissue or cell-specific construct that has been cloned therein. Thus, an Adenoviral vector may include any of the engineered vectors that comprise Adenoviral sequences.

An adenovirus expression vector according to the present invention comprises a genetically engineered form of the adenovirus. The nature of the adenovirus vector is not believed to be crucial to the successful practice of the invention. The adenovirus may be of any of the known serotypes and/or subgroups A–F. Adenovirus type 5 of subgroup C is the preferred starting material in order to obtain one adenovirus vector for use in the present invention. This is because adenovirus type 5 is a human adenovirus about which a great deal of biochemical and genetic information is known, and it has historically been used for most constructions employing adenovirus as a vector.

Advantages of adenoviral gene transfer include the ability to infect a wide variety of cell types, including non-dividing cells, a mid-sized genome, ease of manipulation, high infectivity and they can be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Adenovirus growth and manipulation is known to those of skill in the art, and exhibits broad host range in vitro and in vivo (U.S. Pat. Nos. 5,670,488; 5,932,210; 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Although adenovirus based vectors offer several unique advantages over other vector systems, they often are limited by vector immunogenicity, size constraints for insertion of recombinant genes, low levels of replication, and low levels of transgene expression. A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al., describe the preparation of a replication-defective adenovirus vector, claimed to eliminate the potential for the inadvertent generation of a replication-competent adenovirus (U.S. Pat. No. 5,824,544). The replication-defective adenovirus method comprises a deleted E1 region and a relocated protein IX gene, wherein the vector expresses a heterologous, mammalian gene.

A common approach for generating adenoviruses for use as a gene transfer vector is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210).

Of course, in particular embodiments of the present invention, it is contemplated that low molecular weight or modified hyaluron or vitreous may be used in treatment of such inadvertently produced replication-competent adenovirus. As stated above, vectors contemplated for use in the present invention are replication defective. However, approaches involving replication competent adenoviral vectors, leading to so-called amplification are also contemplated. Thus, particular embodiments are contemplated in which the extent and rate of amplification of replication competent adenoviral vectors is modulated through the application of low molecular weight or modified hyaluron or vitreous.

A class of chimeric adenoviral vector (AdV5/F35, for example) has been created that is capable of delivery of transgenes to hematopoietic progenitors cells. AdV5/F35 vectors are highly effective at transfering transgenes to primitive progenitor cells (Yotnda et al., 2001). These vectors are also capable of infecting the hoechst negative 'side population' of marrow cells. Immunomodulatory genes delivered by these vectors are capable of transduction and some levels of expression over about 5 days. In a preferred embodiment of the present invention cells wherein a transgene has been introduced by such chimeric adenoviral vectors, exemplified but not limited to AdV5/F35, are treated with hyaluron sufficient to enhance transgene expression.

3. Gene Therapy with Adenovirus and Adenoviral and Related Vectors.

In certain preferred embodiments, the inventors contemplate the use of hyaluron or vitreous and related compounds to enhance the expression of transgenes introduced into cells for the purposes of gene therapy.

Gene therapy generally involves the introduction into cells of transgenes whose expression results in amelioration or treatment of disease or genetic disorders. The transgenes involved may be those that encode proteins, structural or enzymatic RNAs, inhibitory products such as antisense RNA or DNA, or any other gene product. Expression is the generation of such a gene product or the resultant effects of the generation of such a gene product. Thus, enhanced expression includes the greater production of any transgene product or the augmentation of that product's role in determining the condition of the cell, tissue, organ or organism. The delivery of transgenes by adenoviral vectors involves what may be termed transduction of cells. As used here, transduction is defined as the introduction into a cell a transgene or transgene construct by an adenoviral or related vector.

Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), and various cancers such as colorectal (Dorai et al., 1999), bladder (Irie et al., 1999), prostate (Mincheff et al., 2000), head and neck (Blackwell et al., 1999), breast (Stewart et al., 1999), lung (Batra et al., 1999) and ovarian (Vanderkwaak et al., 1999). In particular embodiments of the present invention, high molecular weight hyaluron or vitreous is employed in the enhancement of expression of the transgenes delivered by adenoviral vectors.

Thus, the objects of this invention may be accomplished by enhanced expression of a therapeutic gene contained within a gene delivery system, such as a recombinant adenoviral vector delivery system, formulated such that a transduced cell is exposed to the expression-enhancing agent, such as high molecular weight hyaluron or vitreous, and results in the enhanced expression of the therapeutic gene.

The transduced cell may exist in cell culture or in vivo. In vivo, cells as contemplated in the present invention may be located in any tissue or organ of the relevant organism. A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, CD34$^+$ cells CD4$^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

In certain embodiments, the host cell or tissue may be comprised in at least one organism. In certain embodiments, the organism may be, human, primate or murine. In other embodiments the organism may be any eukaryote or eukaryotic cell susceptible to infection or transduction by adenovirus and related viruses or adenoviral vectors. One of skill in the art would further understand the conditions under which to incubate all of the above described host cells to maintain them and to permit their division to form progeny.

Gene therapy strategies have been developed for cancer therapy. Distinct approaches have been developed to treat neoplasms based on gene transfer methods. Methods have been developed to correct specific lesions at defined genetic loci which give rise to neoplastic transformation and progression (Spandidos et al., 1990; Banerjee et al., 1992). Overexpression of dominant oncogenes may be addressed using techniques to inhibit the transforming gene or gene product. Loss of tumor suppressor gene function may be approached using methods to reconstitute wild-type tumor suppressor gene function. Besides these methods to achieve mutation compensation, genetic techniques have been developed to specifically and selectively eradicate tumor cells. These approaches of molecular chemotherapy rely on specific expression of toxin genes in neoplastic cells (Abe et al., 1993). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer, all of which may make use of adenoviral vectors for the tranduction of cells.

Hurwitz, et al. (1999) have described an adenoviral vector containing the herpes simplex thymidine kinase gene that, when transduced into Y79Rb human retinoblastoma cells in vitro, is effective in facilitating the killing of those retinoblastoma cells when treated with the prodrug ganciclovir. A murine model of retinoblastoma, created by the intravitreal injection of Y79Rb cells also responded to trandsduction and treatment. Therefore, gene therapy can effectively reduce the tumor burden in the murine model of human retinoblastoma. Clearly, enhanced expression of the transgene delivered by the adenoviral vector would further enhance the killing effects of the treatment. In particular, the enhancement of adenoviral vector expression within the environment of the eye, i.e. the vitreous would be advantageous. More generally, AdV-TK/ganciclovir suicide gene therapy has been shown to be effective in treating a wide variety of tumors in animal models. See, e.g. Eastham et al., 1996 (prostate); Chen et al., 1994 (brain); Chen et al., 1995 (hepatic); O'Malley et al., 1995 and Goebel et al., 1996 (neck); Behbakht et al., 1996 and Rosenfeld et al., 1996 (ovarian); Esandi et al., 1997 (mesothelioma). Particular embodiments of the present invention include the use of hyaluron in the enhancement or augmentation of AdV-TK/gancilovir gene therapy.

The particular transgene delivered by the adenoviral vector is not limiting and includes those useful for various therapeutic and research purposes, as well as reporter genes and reporter gene systems and contructs useful in tracking the expression of transgenes and the effectiveness of adenoviral and adenoviral vector transduction. Thus, by way of example, the following are classes of possible genes whose expression may be enhanced by using the compositions and methods of the present invention: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, hyaluron synthases, galactosidases, glucanases, glucose oxidases, GTPases, helicases, hemicellulases, hyaluronidases, integrases, invertases, isomersases, kinases, lactases, lipases, lipoxygenases, lyases, lysozymes, pectinesterases, peroxidases, phosphatases, phospholipases, phophorylases, polygalacturonases, proteinases and peptideases, pullanases, recombinases, reverse transcriptases, topoisomerases, xylanases), and reporter genes (e.g. Green fluorescent protein and its many color variants, luciferase, CAT reporter systems, Beta-galactosidase, etc.).

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

p53 currently is recognized as a tumor suppressor gene. High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino-acid phophoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are know to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through $G_1$. The activity of CDK4 is controlled by an activating subunit, D-type cylcin, and by an inhibitory subunit $p16^{INK4}$. The $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in the hyperphosphorylation of the Rb protein. p16 is also known to regulate the function of CDK6.

$p16^{INK4}$ belongs to a newly described class of CDK-inhibitory proteins that also include $p15^{INK4B}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al, 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type $p16^{INK4}$ function by transfection with a plasmid expression vector reduced colony formation by some human cancer cell lines (Okamoto, 1994; Arap, 1995). Delivery of p16 with adenovirus vectors inhibits proliferation of some human cancer cell lines and reduces growth of human tumor xenografts.

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, (Cheung et al., 1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, (Giancotti and Ruoslahti 1990) demonstrated that increasing expression of α5β1 integrin by gene transfer can reduce tumorigenicity of Chinese hamster ovary cells in vivo. C-CAM now has been shown to suppress tumor growth in vitro and in vivo.

Melanoma differentiation-associated (MDA) genes correlate with or directly influence human melanoma cell growth and differentiation (Su et al., 1998). Recent studies have demonstrated that the anti-tumorigenic activity of the MDA family members is not limited to melanomas. The expression of MDA-7 inhibited the growth of glioblastoma, osteosarcoma, colorectal cancer, breast cancer, cervical cancer and nasopharyngeal cancer in vitro (Jiang et al., 1996). MDA-7 expression suppressed the growth in human breast cancer cells in vitro by inducing apoptosis and in vivo in a xenograft model (Su et al., 1998).

Other tumor suppressors that may be employed according to the present invention include BRCA1, BRCA2, zac1, p73, MMAC-1, ATM, HIC-1, DPC-4, FHIT, NF2, APC, DCC, PTEN, ING1, NOEY1, NOEY2, PML, OVCA1, MADR2, WT1, 53BP2, and IRF-1.

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

4. Hyaluron

Hyaluron has many properties that may be advantageous in other medical treatments and in biological processes. Indeed, the use of hyaluron in treatment of disease, infection, and in other uses is widespread. These uses range from simple lubrication, to delivery of drugs, to treatment of retroviral infection. See, for example, U.S. Pat. Nos. 6,194, 392; 6,218,373; 6,271,216; 4,840,941. Also see Hoekstra (1999) and Lee and Spicer (2000).

Hyaluron, Hyaluronan, or Hyaluronic acid, is a naturally occurring polysaccharide (glycosaminoglycan) formed by a repeating unit of glucoronic acid and N-acetyl-glucosamine linked via a Beta 1–3 glycosidic bond. These units are linked through Beta 1–4 glycosidic bonds to form an unbranched molecular chain. The chain is negatively charged when the carboxyl group of the glucuronic acid is dissociated. Under physiological pH it occurs as the salt sodium hyaluronate. Hyaluron is extremely capable at holding water.

The molecular weight and concentration of hyaluron in the vitreous of the eye may vary depending upon the species of organism in which it occurs, the location of the hyaluron in the eye, and means by which its molecular weight is analyzed. Thus, hyaluron's molecular weight may vary from 50,000 Da upwards, and it forms highly viscous solutions. It is one of the most abundant compounds in the human body, and is employed generally in the extracellular matrix to support and protect cells. It is present in all body fluids, but most especially in the vitreous humor of the eye, joint synovia, and umbilical cord. Hyaluron is hydrophilic and very lubricating.

The Merck Index Specifies that Hyaluronic Acid has a Molecular Weight within the range of 50,000 to $8 \times 10^6$ Daltons (Da) depending on source, methods of preparation and methods of determination. The Merck Publication teaches hyaluronic acid as an ophthalmological surgical aid. U.S. Pat. No. 4,801,619 discloses hyaluronic acid administered intra-articularly having a molecular weight of about $3 \times 10^6$ Da or more.

Hyaluron may be isolated from vertebrate tissues (e.g. human umbilical cords, rooster combs) or from cultures of producing strains of bacteria. Various grades of hyaluronic acid may be commercially obtained. See, for example, Sigma catalog entry under Hyaluronic acid. A highly pure, non-inflammatory form is described in U.S. Pat. No. 4,141,973. A commercial product, Healon™ is available from Pharmacia AB (Uppsala, Sweden). The hyaluron of this preparation is said to have a molecular weight exceeding 750,000 Da (and may further exceed 1,200,000 Da) and is suggested for therapeutic use in various articular conditions.

There are a large number of hyaluron producers around the world. These include Anika (Woburn, Mass.), Biomatrix Inc. (Ridgefield, N.J.), Bio-Technology General Corp. (Iselin, N.J.), Fidia Advanced Biopolymers (Brindisi, Italy), Genzyme Corp. (Framingham, Mass.), Kibun Food Chemifa Co. (Tokyo, Japan), Lifecore Biomedical (Chaska, Minn.), and Seikagaku Corp. (Tokyo, Japan).

The natural synthesis of the low molecular weight precursors of the high molecular weight polymer hyaluron is thought to occur by hyalocytes. High molecular weight hyaluron is formed in the extracellular spaces, in most cases by the action of hyaluron synthases. A wide variety of hyaluron synthases exist and may be of use in the creation of high molecular weight forms from lower molecular weight precursors (Spicer and McDonald, 1998). Hyaluron synthase activity may be readily assayed (Spicer, 2001).

High molecular weight hyaluron may be enzymatically treated, resulting in recovery of derivatives or lower molecular weight forms by the enzyme hyaluronidase, or lyase (EC 4.2.2.1). See U.S. Pat. No. 6,258,791. Hyaluronidases are described generally in Kreil (Protein Sci., 1995, 4: 1666–1669). Hyaluronidase may be derived from a mammalian, reptilian or hymenopteran hyaluronate glycanohydrolase, from a hyaluronate glycanohydrolase from the salivary gland of the leech, or from a bacterial, in particular streptococcal, pneumococcal and clostridial hyaluronate lyase. Hyaluronidases are widely available from commercial suppliers. See, for example, Hyaluronidase entry in Sigma-Aldrich (2002).

5. Uses of Hyaluron or Vitreous in Modulating Adenoviral Mediated Gene Expression and Adenovirus Infection.

The inventors have made the surprising and unexpected discovery that derivatives of high molecular weight hyaluron, i.e. low molecular weight hyaluron, high molecular weight hyaluron that is "out of date," high molecular weight hyaluron that has been treated with lyase or hyaluronidase, or vitreous that has been so treated, significantly inhibits transduction of cells by adenovirus and adenoviral vectors. This unexpected property of these compositions enables the treatment of adenoviral infection, infection by replication competent adenoviral vectors and the modulation of adenoviral vector transduction.

Low molecular weight hyaluron, as contemplated in the present invention, comprises the products of high molecular weight hyaluron exposed to conditions that degrade the high molecular weight form or vitreous. Such degradation may be accomplished through enzymatic treatment or through exposure of the high molecular weight form of hyaluron or vitreous to air for a sufficient period of time, or by selecting hyaluron or vitreous that is older than its allowed date of clinical use. The products of such degradation may be recognized through comparison of intact, unmodified, or fresh high molecular weight hyluron and the degradative products when analyzed by the methods of gel electrophoresis.

In particular, a non-limiting example of such a comparison comprises the electrophoresis of the relevant samples through 0.5% agarose in 1× Tris Acetate EDTA buffer (TAE, see Sambrook 2001). The samples may be loaded into wells in the agarose gel using 7 volumes of sample added to one volume of 8× Loading Buffer (2 M sucrose; 1.5 M NaCl) and exposed to 80 to 100 volts for from 4 to 6 hours. After electrophoresis, the hyaluron samples are treated with 0.005% StainsAll™ (4,5,4',5'-Dibenzo-3,3'-diethyl-9-methyl-thiacarbocyanine bromide; 3,3'-Diethyl-9-methyl-4,5,4',5'-dibenzothiacarbocyanine; 1-Ethyl-2-[3-(3-ethylnaphtho[1,2-d]thiazolin-2ylidene)-2-methylpropenyl]naphtho[1,2-d]thiazolium bromide, Sigma-Adrich Co., Inc.) in 50% ethanol in the dark for 12 hours or overnight. The gel may then be washed with water to remove unbound stain. The hyaluron can be visualized by exposing the so-treated gel to light for 30 minutes. As will be appreciated by those of skill in the art, other methods of comparing the molecular weight and other properties of hyaluron samples are known to those of skill in the art and may be employed in the context of the present invention in order to identify those samples that are effective in inhibiting adenoviral infection or adenoviral vector mediated transgene expression.

In particular, the inventors herein provide for a method of screening for the appropriate hyaluron sample for use as an inhibitor or enhancer of adenoviral infection or adenoviral mediated transgene expression. Thus, samples of high molecular weight hyaluron, or high molecular weight hyaluron exposed or treated so as to produce lower molecular weight or other derivatives may be screened for their ability to inhibit adenoviral mediated transgene expression or adenoviral infection. Such a screening process typically proceeds through comparison of the effects of such samples upon adenoviral mediated gene expression or infection in relation to compositions of known effect on adenoviral mediated gene expression or infection as provided in the present description and in the examples provided.

A typical, but non-limiting example would include the contacting of a composition comprising the suspect sample with cells transduced by adenoviral vector or adenovirus or to be infected by adenovirus and, likewise, the contacting of a composition comprising a sample of known effects upon adenoviral mediated gene expression or infection (e.g. high molecular weight hyaluron or vitreous as provided herein) with equivalent cells. The effects of the contacting with the samples are compared, using any number of means available for determining the infectivity, transduction rate, or levels of gene expression. Inhibition of adenoviral infection or transgene expression is indicated by a reduced level of infection or gene expression in the suspect sample. Likewise, samples may be assayed for their ability to enhance transgene expression.

The levels of transgene expression may be determined through means derived to specifically measure the presence of the particular transgene involved, such as antibodies, enzymatic assays, and the like.

In particular embodiments, the treatment of adenoviral infection comprises treating cell(s), tissue(s), organ(s), or individual organism with sufficient amounts of an adenoviral inhibitor so as to inhibit existing infection, prevent the spread of infection to other cells, or to prevent the initial infection of any cell. Said inhibitor may comprise hyaluron derivatives, low molecular weight hyaluron, "out of date" hyaluron, "out of date" vitreous, or vitreous treated with hyaluronidase and the like.

The contacting of the cell with low molecular weight hyaluron or derivatives of high molecular weight hyaluron or vitreous may occur after the cell has been contacted with vector or virus, after a period of time has elapsed since the cell was first contacted with vector or virus, or substantially contemporaneously with the infection of the cell. The period of time that may elapse since the cell was contacted with vector or virus and the contacting of the cell with low molecular weight hyaluron or derivatives of high molecular weight hyaluron or vitreous may range from a few seconds, to several or many minutes, to several hours. Thus, this elapsed time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds or less. Similarly, this elapsed time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes or less. Likewise, this elapsed time period may be 1, 2, 3, 4, 5, 6, 7, 8, 9, 10, 11, 12, 13, 14, 15, 16, 17, 18, 19, 20, 21, 22, 23, or 24 hours and any range derivable therein.

The period of time over which the cell is contacted by low molecular weight hyaluron or derivatives of high molecular weight hyaluron or vitreous may range from a few minutes or less to several hours or more. Thus, the time period over which the cell is contacted cell may be may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds or less. Similarly, this time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes or less. Likewise, this contacting time period may be 1, 2, 3, 4, 5, 6, 7, 8, 9, or 10, 11, 12, 13, 14, 15, 16, 17, 18, 19, 20, 21, 22, 23, 24 or more hours, and any range derivable therein. It is specifically contemplated that cells may be contacted by low molecular weight hyaluron or derivatives of high molecular weight hyaluron or vitreous for one or many days.

The concentrations at which low molecular weight hyaluron or derivatives of high molecular weight hyaluron or vitreous is applied may range from less than 10 micrograms per 100 microliters to at least 240 micrograms per 100 microliters or more. Thus, the amount of low molecular weight hyaluron or derivatives of high molecular weight hyaluron or vitreous per 100 microliters of solution may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 150, 200, 240, micrograms or more and any range derivable therein.

Clearly, when the objective is treatment of adenoviral infection or infection by replication competent adenoviral vectors the particular time of treatment and time period over which treatment occurs will be determined by appropriate medical practice and experience.

In order to increase the effectiveness of low molecular weight hyaluron or derivatives of high molecular weight hyaluron or vitreous, it may be desirable to combine these compositions and methods of the invention with an agent effective in the treatment of other diseases or disorders. In some embodiments, it is contemplated that a conventional therapy or agent, including but not limited to, a pharmacological therapeutic agent, a surgical therapeutic agent (e.g., a surgical procedure) or a combination thereof, may be combined with administration of low molecular weight hyaluron or derivatives of high molecular weight hyaluron or vitreous. Thus, in certain embodiment, a therapeutic method of the present invention may comprise administration of low molecular weight hyaluron or derivatives of high molecular weight hyaluron or vitreous of the present invention in combination with another therapeutic agent.

This process may involve contacting the cell(s) with an agent(s) and the low molecular weight hyaluron or derivatives of high molecular weight hyaluron or vitreous at the same time or within a period of time wherein separate administration of the low molecular weight hyaluron or derivatives of high molecular weight hyaluron or vitreous and an agent to a cell, tissue or organism produces a desired therapeutic benefit. The terms "contacted" and "exposed," when applied to a cell, tissue or organism, are used herein to describe the process by which a therapeutic construct or therapeutic agent are delivered to a target cell, tissue or organism or are placed in direct juxtaposition with the target cell, tissue or organism. The cell, tissue or organism may be contacted (e.g., by adminstration) with a single composition or pharmacological formulation that includes both low molecular weight hyaluron or derivatives of high molecular weight hyaluron or vitreous and one or more agents, or by contacting the cell with two or more distinct compositions or formulations, wherein one composition includes low molecular weight hyaluron or derivatives of high molecular weight hyaluron or vitreous and the other includes one or more agents.

The administration of low molecular weight hyaluron or derivatives of high molecular weight hyaluron or vitreous may precede, be co-current with and/or follow the other agent(s) by intervals ranging from minutes to weeks. In embodiments where the low molecular weight hyaluron or derivatives of high molecular weight hyaluron or vitreous, and other agent(s) are applied separately to a cell, tissue or organism, one would generally ensure that a significant period of time did not expire between the time of each delivery, such that the low molecular weight hyaluron or derivatives of high molecular weight hyaluron or vitreous and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the low molecular weight hyaluron or derivatives of high molecular weight hyaluron or vitreous. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1 week, about 2 weeks, about 3 weeks, about 4 weeks, about 5 weeks, about 6 weeks, about 7 weeks, about 8 weeks, about 1 month, about 2 months, about 3 months, about 4 months, about 5 months, about 6 months, about 7 months, about 8 months, about 9 months, about 10 months, about 11 months, or about 12 months, and any range derivable therein, prior to and/or after administering the low molecular weight hyaluron or derivatives of high molecular weight hyaluron or vitreous.

Various combination regimens of the low molecular weight hyaluron or derivatives of high molecular weight hyaluron or vitreous and one or more agents may be employed. Non-limiting examples of such combinations are shown below, wherein a composition comprising low molecular weight hyaluron or derivatives of high molecular weight hyaluron or vitreous is "A" and an agent is "B":

A/B/A B/A/B B/B/A A/A/B A/B/B B/A/A A/B/B/B B/A/ B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the composition comprising low molecular weight hyaluron or derivatives of high molecular weight hyaluron or vitreous to a cell, tissue or organism may follow general protocols for the administration of therapeutics, taking into account the toxicity, if any. It is expected that the treatment cycles would be repeated as necessary. In particular embodiments, it is contemplated that various additional agents may be applied in any combination with the present invention.

Compositions for modulation of transgene expression include solutions of hyaluron or vitreous in various combinations. Hyaluron or vitreous may be delivered to cells, tissues, etc. in combination with various compatible media. These include, but are not limited to serum-free cell culture media and water. Contemplated embodiments include any other suitable diluent or media that is compatible with hyaluron, or other media or diluent that is compatible with vitreous. As described below, such compositions may include other components added for various purposes, such as preservation, etc., as long as they do not detract from the effects of the active components provided herein.

The inventors have made the surprising and unexpected discovery that high molecular weight hyaluron or vitreous significantly enhances the expression of transgenes introduced by adenovirus and adenoviral vectors. This unexpected property of these compositions enables the modulation of transgenes introduced by adenovirus and adenoviral and related vectors. In particular embodiments, cells are contacted with high molecular weight hyaluron or vitreous such that expression of adenoviral transgenes is enhanced.

The contacting of the cell with high molecular weight hyaluron or vitreous may occur after the cell has been contacted with vector or virus, after a period of time has elapsed since the cell was first contacted with vector or virus, or substantially contemporaneously with the transduction of the cell. The period of time that may elapse since the cell was contacted with vector or virus and the contacting of the cell with high molecular weight hyaluron or vitreous may range from a few seconds, to several or many minutes, to several hours. Thus, this elapsed time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds or less. Similarly, this elapsed time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes or less. Likewise, this elapsed time period may be 1, 2, 3, 4, 5, 6, 7, 8, 9, or 10 hours and any range derivable therein.

The period of time over which the cell is contacted by high molecular weight hyaluron or vitreous may range from a few minutes or less to several hours or more. Thus, the time period over which the cell is contacted cell may be may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds or less. Similarly, this time period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes or less. Likewise, this contacting time period may be 1, 2, 3, 4, 5, 6, 7, 8, 9, or 10, 11, 12, 13, 14, 15, 16, 17, 18, 19, 20, 21, 22, 23, 24 or more hours, and any range derivable therein. It is specifically contemplated that cells may be contacted by high molecular weight hyaluron or vitreous for one or many days.

The concentrations at which high molecular weight hyaluron or vitreous is applied may range from less than 10 micrograms per 100 microliters to at least 100 micrograms per 100 microliters or more. Thus, the amount of high molecular weight hyaluron or vitreous per 100 microliters of solution may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 micrograms or more. Similarly, these concentrations may be expressed as percents, weight per volume.

Compositions for modulation of transgene expression include solutions of high molecular weight hyaluron or vitreous in various combinations. High molecular weight hyaluron or vitreous made by delivered to cells, tissues, etc. when presented in combination with various compatible media. These include, but are not limited to serum-free cell culture media and water. Contemplated embodiments include any other suitable diluent or media that is compatible with hyaluron, or other media or diluent that is compatible with vitreous. As described below, such compositions may include other components added for various purposes, such as preservation, etc., as long as they do not detract from the effects of the active components provided herein.

6. Pharmaceutical Preparations

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Pharmaceutical compositions of the present invention comprise an effective amount of hyaluron or vitreous alone or in the presence of an additional agent (for example, an adenoviral vector) dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one adenoviral vector, hyaluron, vitreous or additional active ingredient will be known to those of skill in the art in light of the present disclosure, as exemplified by Remington's Pharmaceutical Sciences, 18th Ed. Mack Printing Company, 1990). Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329). Except insofar as any conventional carrier is incompatible with the active ingredient, its use in the therapeutic or pharmaceutical compositions is contemplated.

The compositions of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The hyalurons of the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the compositions of the present invention are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

U.S. Pat. No. 4,808,576 dislcoses that hyaluronic acid, an agent well known to reduce the sequeulae of trauma in mammalian joint tissue when applied directly to the traumatized tissue, will be carried to such traumatized tissue by the mammal's natural processes if applied at a site remote from the traumatized tissue. Thus, hyaluronic acid in any therapeutically acceptable form can, according to the patent, be administered by the typical remote routes including intravenous, intramuscular, subcutaneous and topical. This property may make the utilization of hyaluronic acid much more convenient and attractive. For instance the treatment of arthritis in horse or human joints with hyaluronic acid according to the patent would no longer require more difficult intra articular injections.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, collagen, aluminum monostearate, gelatin or combinations thereof.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methodology Employed in Examples 1-5.

Cell Lines

WERI-Rb cells (derived from human retinoblastomas), Jurkat cells (human acute T-cell lymphoma), Jurkat cells engineered to express CD44, and HeLa cells (human cervical epitheloid carcinoma) were maintained in culture using Minimal Essential Medium supplemented with 5% FCS. The Jurkat-CD44 cell line was established by transfection (using CellFECTIN™, GibcoBRL) of Jurkat cells with a plasmid containing a CD44 minigene (Brian Seed, Harvard University). After 72 hours, the CD44-expressing cells were selected using G418 (800 μg/ml) and stable cell lines were established by dilutional cloning. EpH4 cells (murine epithelial cells provided by L. Huber, IMP, Vienna, Austria) were cultured in Dulbeco's Minimal Essential Medium supplemented with 10% FBS and glucose (4.5 g/l). Serum can be shown to have an effect on adenoviral-mediated transgene expression, however this effect is not as potent as vitreous nor is the serum effect inhibited by lyase digestion. The experiments reported here were performed using cells cultured in the absence of serum or at 0.5% serum to isolate the effects of the vitreous. All cell cultures were maintained at 37° C. in 5% $CO_2$.

Adenoviral Constructs

Adenoviral 5 (AdV) constructs containing either firefly luciferase (AdV-luc) or green fluorescent protein (AdV-GFP) reporter genes or expressing fiber domains from adenovirus 35 (AdV5/F35) were provided by the Center for Cell and Gene Therapy, Baylor College of Medicine. Constructs expressing mutated fiber/knob or penton base domains were provided by T. Wickham (GenVec Corp.).

Antibodies and Reagents

The KM114 monoclonal antibody to the hyaluron binding site of murine CD44 was obtained from BD Biosciences PharMingen. Vitreous was harvested from fresh or frozen bovine eyes (Ladpak Slaughterhouse, Needville, Tex.). The vitreous was sheared using a 19-gauge needle to reduce viscosity and clarified by centrifugation before dilution in serum-free culture medium. Hyaluronic acid (hyaluron) lyase and collagenase were purchased from SIGMA™ (Sigma-Aldrich Co., Inc.). The large molecular weight hyaluron (Healon™, 1% sodium hyaluron) was obtained from Pharmacia, Corp. Expressed luciferase activity was quantitated using the Luciferase Assay System™ (Promega).

EXAMPLE 1

Vitreous Enhances Adenoviral-mediated Transgene Expression

Low concentrations of vitreous markedly enhanced adenoviral-mediated transgene expression when AdV-luc, an adenoviral vector containing the firefly luciferase gene as the reporter, was used to transduce retinoblastoma cell lines. WERI-Rb cells ($1 \times 10^4$ cells/well) were incubated with AdV-luc (200 viral particles (vp)/cell) and 0% (control), 0.1%, 0.5%, 2.5%, and 5% of freshly prepared bovine vitreous for 18 hours. Cells were harvested and assayed for luciferase activity. Cultures were performed in triplicate. FIG. 1 shows that transgene expression increases as a direct function of vitreous concentration. The enhancement was over and above that observed in the presence of serum.

EXAMPLE 2

Hyaluronic Acid Lyase Abrogates Enhancement by Vitreous

To examine the potential role of either collagen or hyaluronic acid, the two major components of vitreous, vitreous was digested with either collagenase or hyaluronic acid lyase prior to incubation with the retinoblastoma cells and viral vector. Vitreous or serum was diluted to 1% in serum-free media and then treated with hyaluron lyase (Strep lytica, 10 units) for 1 hour at 37° C. The treated vitreous or serum was added to WERI-Rb cells ($1.2 \times 10^4$ cells/well) in serum-free media to a final concentration of 0.5%. AdV-luc was added (500 vp/cell) and the cells were cultured for 18 hours. The cells were harvested and luciferase activity was determined.

Figure 2:
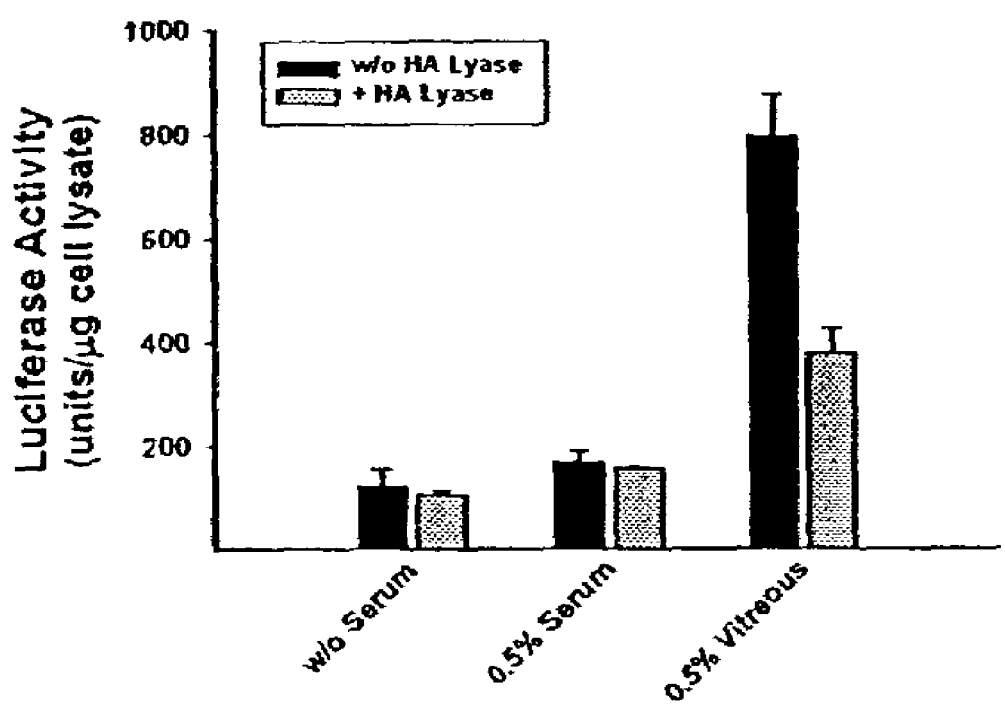
FIG. 2. Hyaluronic acid lyase abrogates vitreous enhanced adenoviral-mediated transgene expression.

Digestion of the vitreous with collagenase had no effect on the enhancement of reporter transgene expression. However, digestion with hyaluronic acid lyase (10 units lyase in 500 microliters of 1% vitreous) abrogated the effect of the vitreous (FIG. 2). Lyase inactivated by boiling did not inhibit vitreous enhanced adenoviral mediated luciferase expression (data not shown).

EXAMPLE 3

Enhanced Expression is not Dependent Upon Adenoviral Binding or Internalization

To determine whether vitreous enhanced adenoviral binding or internalization, adenoviral vector was labeled with $^{35}S$-methionine and then incubated with HeLa cells (known to have both CAR and $\alpha_v$ integrins and to be easily infected by adenovirus) in the presence or absence of 0.5% vitreous. After incubation, the cells were washed and the total radioactivity determined. Over a six hour time-course there was no difference in the amount of $^{35}S$ quantitated indicating that the enhancement was not at the stage of binding or internalization but rather at some subsequent step in transgene expression (data not shown).

Figure 3:
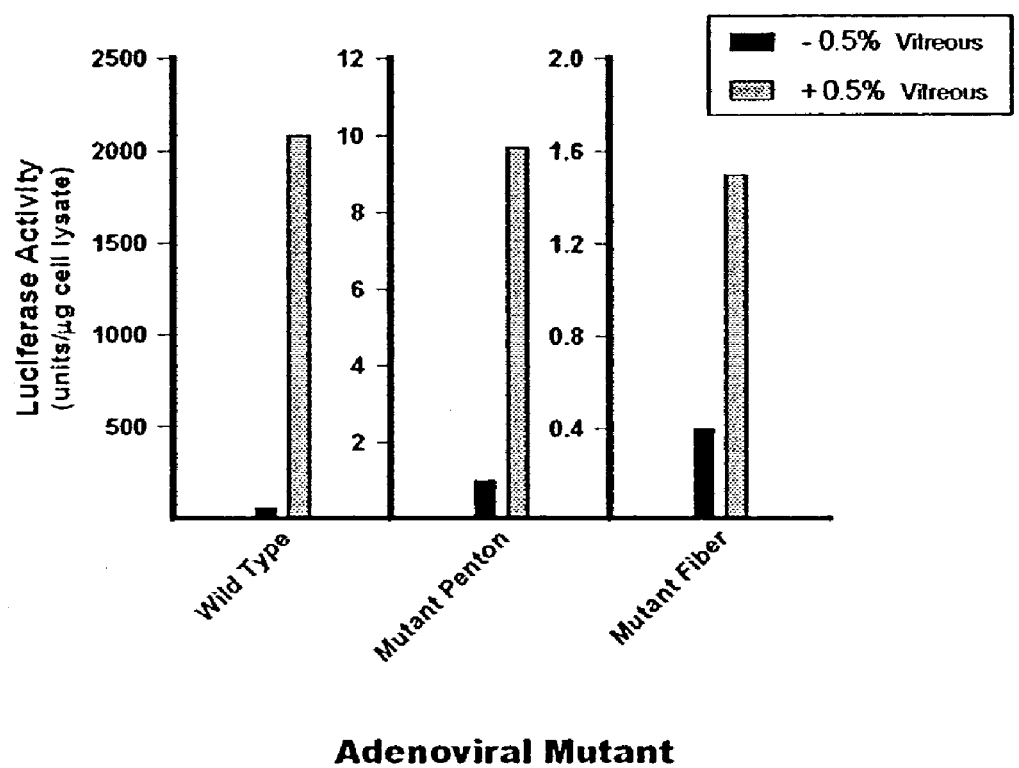
FIG. 3. Enhanced transgene expression is not dependent on adenoviral binding or internalization.

Using adenoviral vectors in which either the fiber/knob protein or the penton base protein was mutated strengthened these conclusions. WERI-Rb cells ($1 \times 10^4$ cells/well) were incubated for 18 hours in serum-free media with either wild type, mutant penton or mutant fiber variants of adenovirus (1000 vp/cell) in the presence or absence of 0.5% vitreous. Cells were harvested and luciferase activity was determined. Disruption of adenoviral binding (mutated fiber/knob) or internalization (mutated penton base) domains reduced the ability of adenovirus to enter the cell but did not inhibit the ability of vitreous to enhance expression of the luciferase transgene (FIG. 3).

Another modified adenoviral vector was used to further confirm these observations. AdV serotype 5 requires the CAR receptor for binding and $\alpha_v$ integrins for internalization; AdV serotype 35 utilizes a different mechanism. The expression of GFP delivered to retinoblastoma cells by AdV 5 engineered to contain AdV 35 fiber proteins (AdV5F35) also increases in the presence of 0.5% vitreous.

Figure 4:
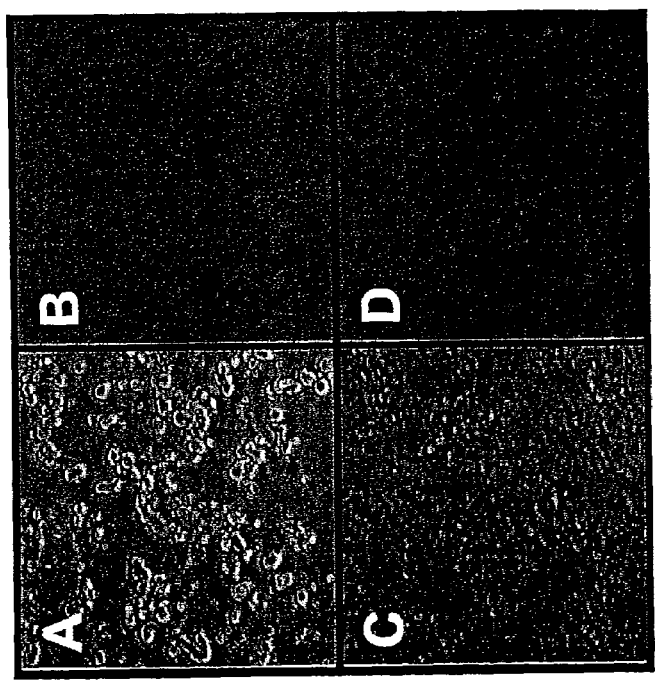
FIGS. 4A, 4B, 4C, and 4D. Vitreous enhances adenoviral-mediated transgene expression in cells transduced using an alternate adenoviral receptor. WERI-Rb cells ($1 \times 10^4$ cells/well) were incubated in serum-free media with (C,D) or without (A,B) 0.5% vitreous. The cells were transduced at a ratio of 5 vp/cell with a chimeric adenovirus (AdV5/F35) in which the fiber/knob domains of AdV35 replaced the fiber/knob domains of AdV5. Bright field (A,C) and fluorescent (B,D) photographs of representative fields are shown.

WERI-Rb cells ($1 \times 10^4$ cells/well) were incubated in serum-free media with (C,D) or without (A,B) 0.5% vitreous. The cells were transduced at a ratio of 5 vp/cell with a chimeric adenovirus (AdV5/F35) in which the fiber/knob domains of AdV35 replaced the fiber/knob domains of AdV5. Bright field (A,C) and fluorescent (B,D) photographs of representative fields are shown (FIG. 4). Therefore, as long as the adenovirus can bind and internalize, vitreous can enhance transgene expression regardless of the receptors used.

EXAMPLE 4

Time Dependence of Vitreous Enhancement

Figure 5:
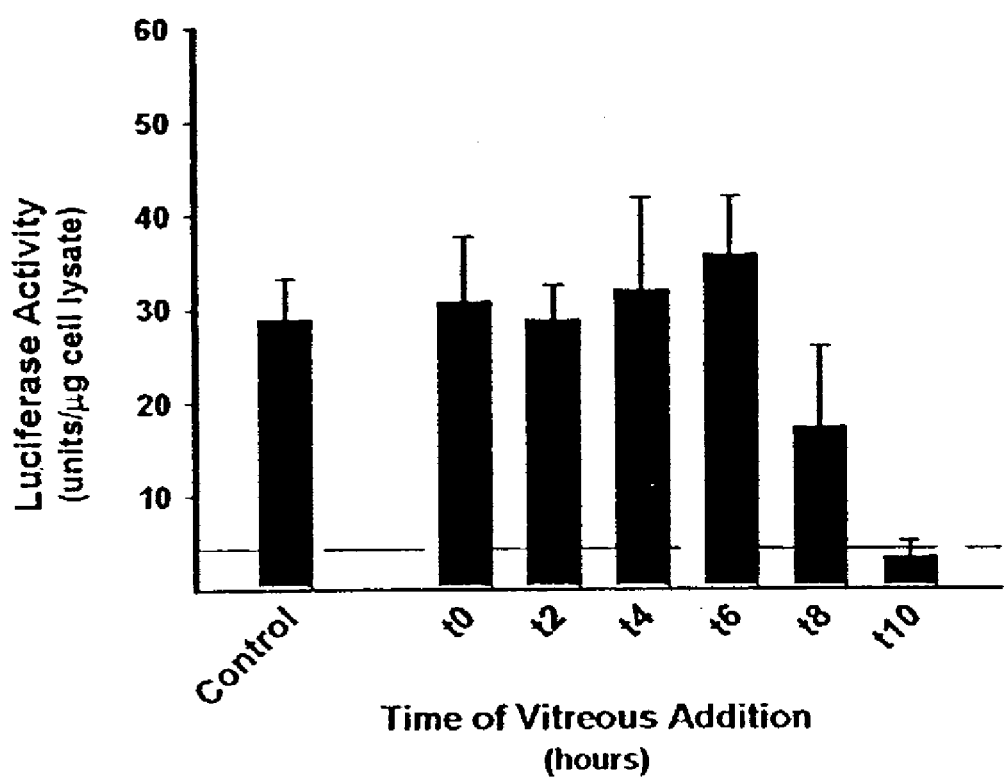
FIG. 5. Vitreous-mediated enhancement of transgene expression: Time dependence of vitreous addition. The reference line indicates baseline transgene expression in the absence of vitreous.

WERI-Rb cells were incubated with AdV-luc (200 vp/cell) in serum-free media for 2 hours to allow time for the virus to bind and internalize. The cells were washed, resuspended in fresh serum-free media, and aliquoted into wells of a 96-well microtiter plate at $1\times10^4$ cells/well. Vitreous was added at a final concentration of 0.5% at the times indicated. Luciferase assays were performed 20 hours after AdV-luc addition. Maximum enhancement of adenoviral-mediated transgene expression could be obtained if the vitreous was added at least 6 hours after the adenovirus was removed (FIG. 5).

Figure 6:
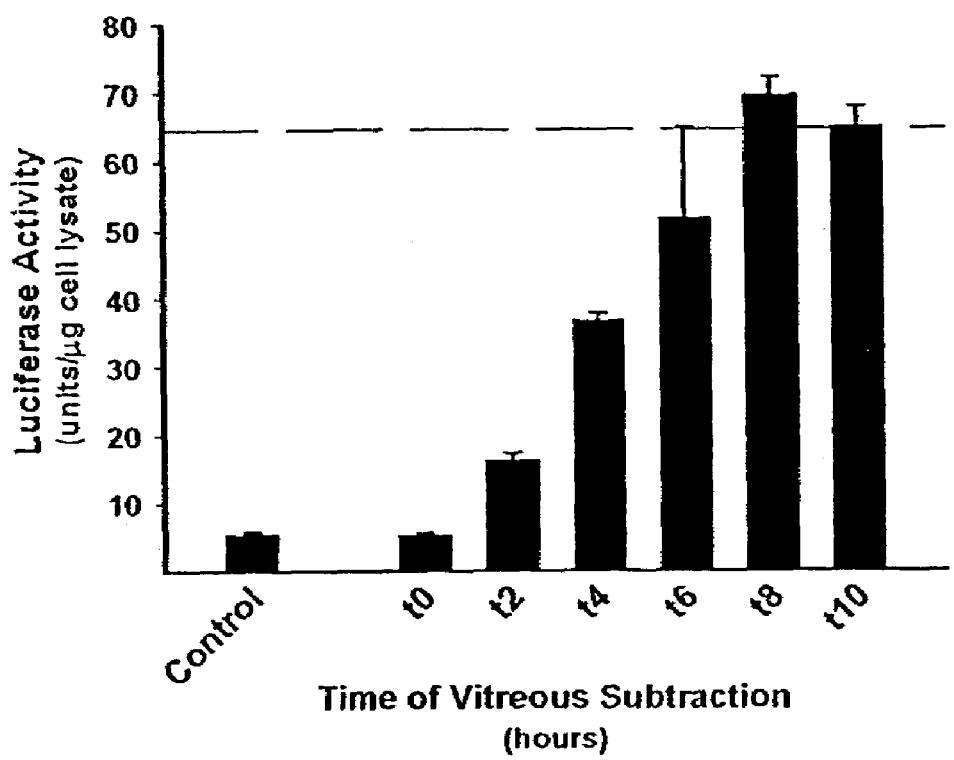
FIG. 6. Vitreous-mediated enhancement of transgene expression: Time dependence of vitreous addition. The reference line represents transgene expression in cells continuously exposed to 0.5% vitreous for the entire 20 hour incubation period.

Conversely, vitreous that had been added at the time the adenoviral vector was removed from the culture and then removed at various subsequent time intervals by washing the cells was able to enhance transgene expression for at least 6 hours. WERI-Rb cells were incubated with AdV-luc (200 vp/cell) in serum-free media for 2 hours to allow time for the virus to bind and internalize. The cells were washed, resuspended in fresh serum-free media plus 0.5% vitreous and incubations were continued. At the times indicated, cells were withdrawn, washed, and resuspended in serum-free media before being aliquoted into wells of a 96-well microtiter plate at $1\times10^4$ cells/well. Luciferase assays were performed 20 hours after AdV-luc addition (FIG. 6).

EXAMPLE 5

Hyaluron Enhances Adenoviral-mediated Transgene Expression

Figure 7:
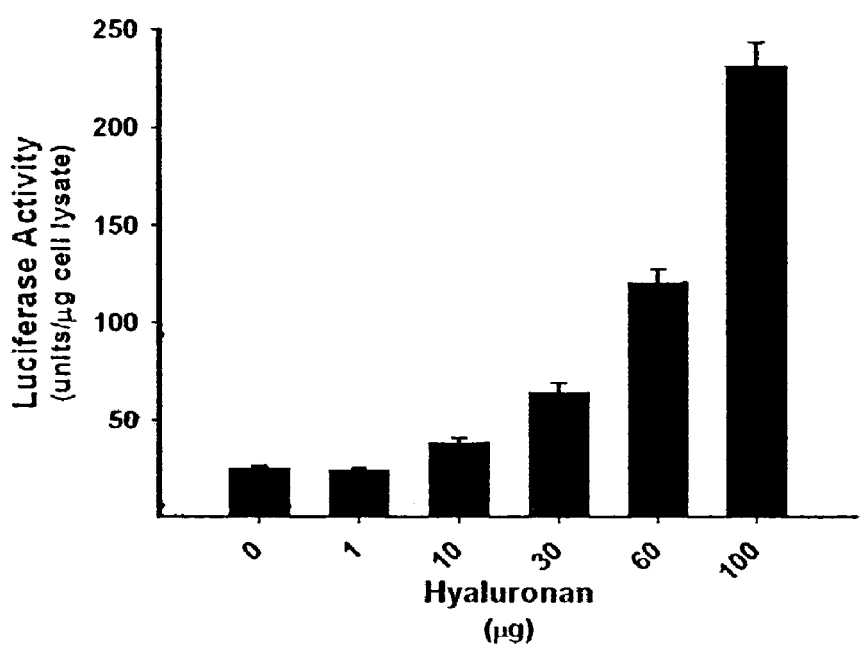
FIG. 7. Activation of adenoviral-mediated transgene expression by hyaluron. Bars represent standard error from the mean.

High molecular weight hyaluron enhances adenoviral delivered transgene expression. WERI-Rb cells $1\times10^4$ cells/well) were incubated with AdV-luc (200 vp/cell) and the concentrations of freshly diluted high molecular weight hyaluron (average M.W. 650,000 kDa) from 0 to 100 micrograms Hyaluron per 100 microliters for 18 hours. Cells were harvested and assayed for luciferase activity. Cultures were performed in triplicate (FIG. 7). Transgene expression may be enhanced up to 20-fold.

EXAMPLE 6

Figure 8:
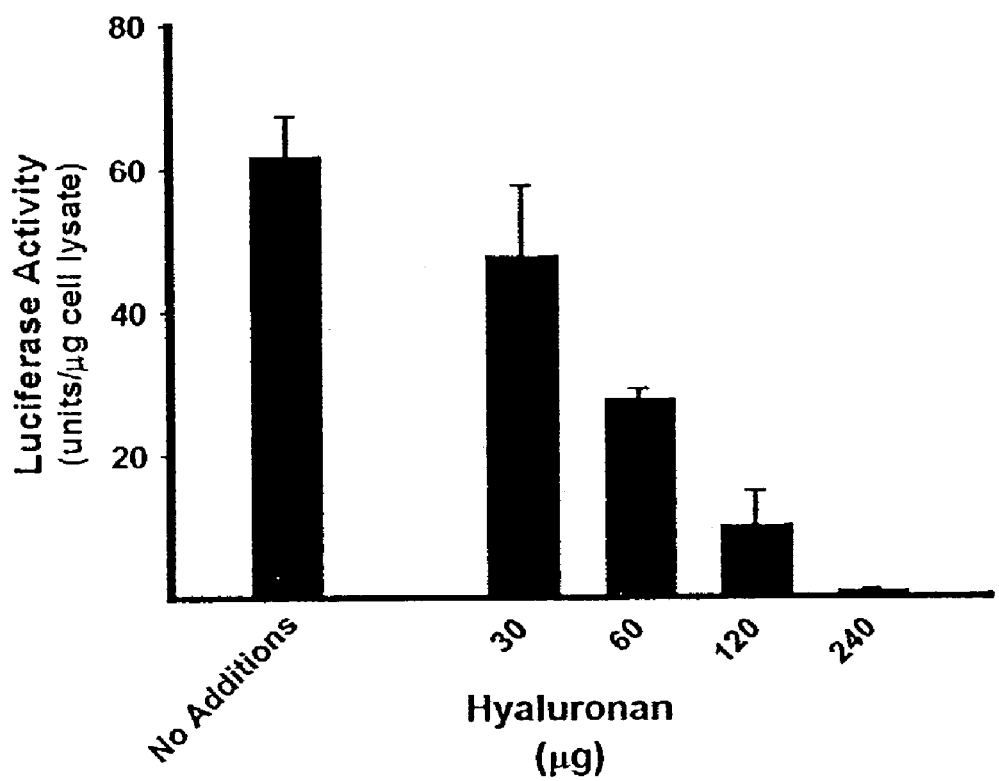
FIG. 8. Inhibition of adenoviral-mediated transgene expression by "outdated" hyaluron. Bars represent standard error from the mean.

Adenovirus Mediated Transgene Expression is Inhibited by Degraded or Modified Hyaluron Hyaluron that had been subjected to limited digestion with lyase not only failed to activate but actually inhibited base-line adenoviral mediated transgene expression. WERI-Rb cells ($1\times10^4$ cells/well) were incubated with AdV-luc (200 vp/cell) and concentrations of "outdated" hyaluron ranging from 0 to 240 micrograms per 100 microliters for 18 hours. Cells were harvested and assayed for luciferase activity. Cultures were performed in triplicate. FIG. 8 shows that even partial digestion by lyase resulted in hyaluron in a conformation that effectively inhibited adenoviral mediated transgene expression.

EXAMPLE 7

CD44 is Involved in the Regulation of Adenoviral-mediated Transgene Expression

Figure 9:
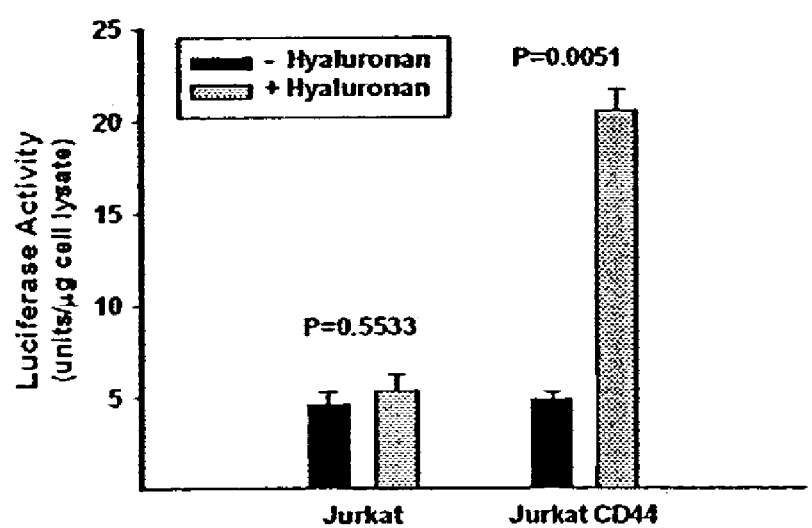
FIG. 9. PMA-activated CD44 is important for enhancement of adenoviral-mediated transgene expression. Bars represent standard error from the mean and significance was determined using the paired Student's t-test.

Since the vitreous-induced enhancement of adenoviral-mediated transgene expression can be abrogated by digestion of the vitreous with hyaluron lyase and can be achieved by purified large molecular weight hyaluron, a potential role for the hyaluron binding receptor CD44 was examined. Jurkat and Jurkat-CD44 cells were incubated with PMA (10 ng/ml) to activate the CD44. The cells were washed, resuspended in serum-free media, and aliquoted at $1\times10^4$ cells/well of a 96 well microtiter plate. AdV-luc (1000 vp/cell) was added and the cells were incubated in the presence or absence of freshly diluted hyaluron (100 micrograms/well) for 18 hours before determination of luciferase activity (FIG. 9). Jurkat cells, which do express CAR but do not express CD44 or other hyaluron-binding receptors and do not express $\alpha_v$ integrins are not easily transduced by AdV5 and are not affected by vitreous (FIG. 9). However, Jurkat cells stably transfected with a CD44 expression plasmid can be transduced by AdV5 and the transgene expression can be enhanced in the presence of hyaluron (FIG. 9).

Figure 10:
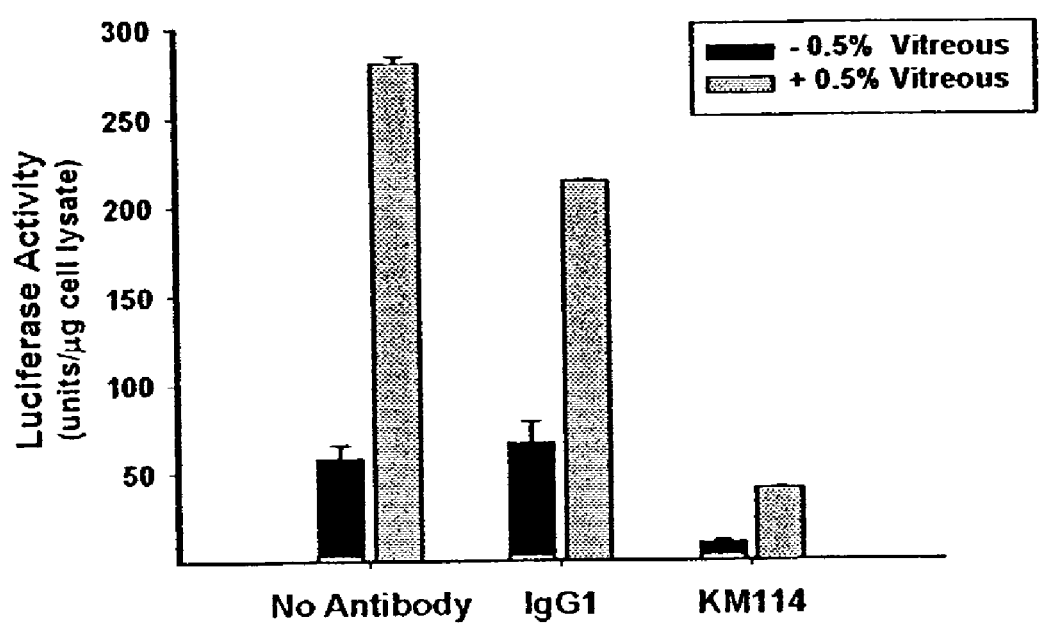
FIG. 10. Anti-CD44 inhibits adenoviral-mediated transgene expression. Bars represent standard error from the mean.
Figure 11:
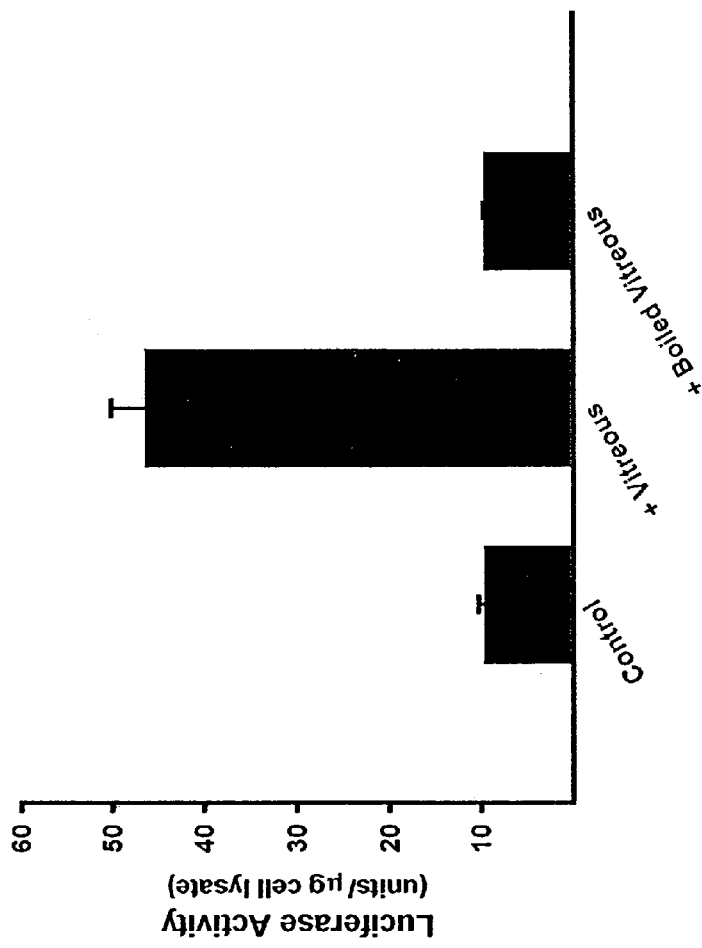
FIG. 11. Effect of boiling Vitreous on enhancement of adenoviral-mediated transgene expression.

To further confirm a role for CD44, an antibody (KM114) to murine CD44 that blocks hyaluron binding was examined to determine its effect on vitreous enhancement. The CD44-expressing murine cell line EpH4 was used as the target cell. Murine EpH4 cells (CD44 positive) were preincubated in serum-free media in the presence of excess KM114, a CD44 specific monoclonal antibody or an isotype-matched IgG1 control antibody. The cells were washed, resuspended in serum-free media, and aliquoted at $1\times10^4$ cells/well of a 96-well microtiter plate. AdV-luc was added (200 vp/cell) and the incubations were continued for 18 hours before luciferase activity was determined. Cultures were performed in triplicate. Vitreous enhanced transgene expression in the presence of an isotype matched control antibody (FIG. 10). Not only vitreous-enhanced transgene expression but also baseline transgene expression was inhibited in the presence of KM114 (FIG. 10). These results confirm a role for CD44 and its ligand hyaluron in the regulation of adenoviral-mediated transgene expression.

EXAMPLE 8

Screening for Forms of Hyaluron

Electrophoresis of the relevant samples is carried out through 0.5% agarose in 1×Tris Acetate EDTA buffer (TAE, see Sambrook 2001). The samples were loaded into wells in the agarose gel using 7 volumes of sample added to one volume of 8× Loading Buffer (2 M sucrose; 1.5 M NaCl) and exposed to 80 to 100 volts for from 4 to 6 hours. After electrophoresis, the gel was treated with 0.005% StainsAll™ (SIGMA™) in 50% ethanol in the dark for 12 hours or overnight, then washed with water to remove unbound stain. The hyaluron was visualized by exposing the treated gel to light for 30 minutes.

Testing of samples for their effects upon adenoviral-mediated transgene expression proceeds an in the materials and methods provided in the above examples. That is, WERI-Rb cells ($1\times10^4$ cells/well) are incubated with AdV-luc (200 vp/cell) and the subject hyaluron samples at concentrations from 0 to 100 micrograms Hyaluron per 100 microliters for 18 hours. Cells are harvested and assayed for luciferase activity.

EXAMPLE 9

Vitreous Rehabilitates Low Molecular Weight Hyaluron

Figure 12:
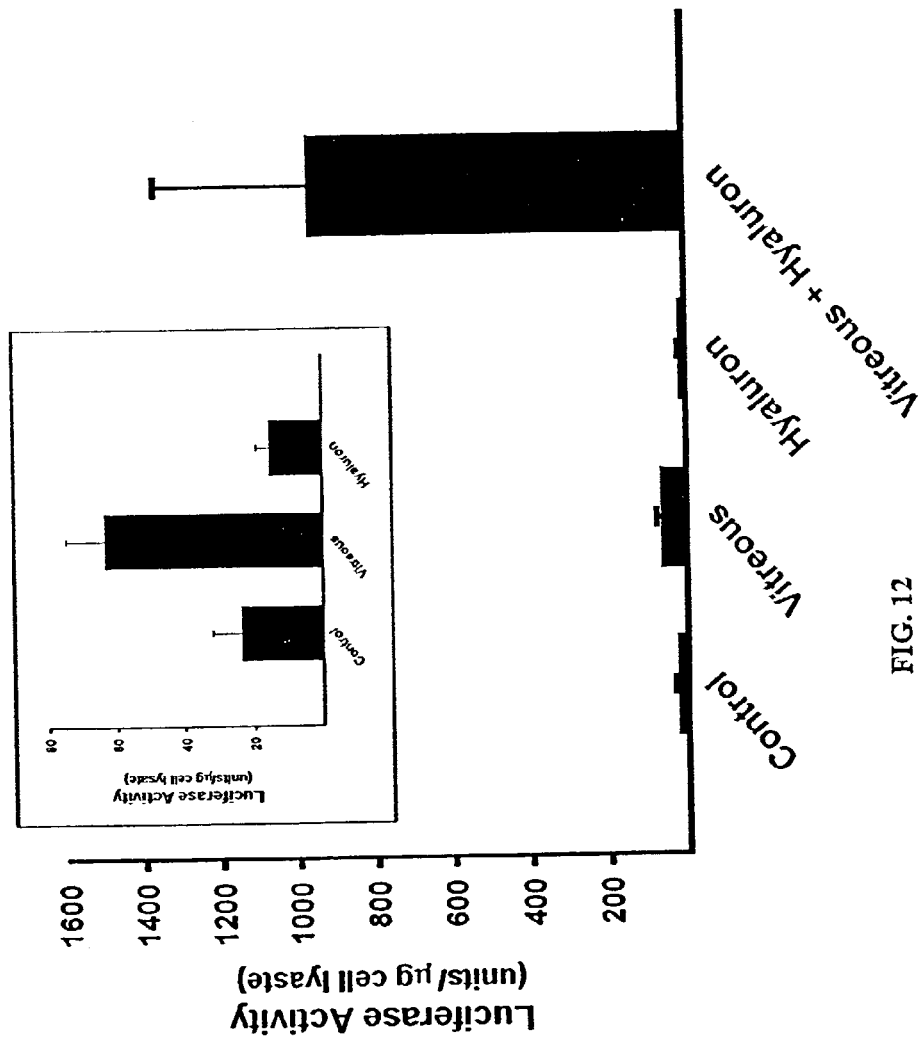
FIG. 12. Effect of combined vitreous and low molecular weight hyaluron on enhancement of adenoviral-mediated transgene expression.

FIG. 12 shows that the enhancing effects of vitreous rehabilitate low molecular weight hyaluron. The effects of the combination of low molecular weight hyaluron and vitreous are multiplicative, resulting in a nearly 1000-fold increase in transgene expression. WERI-Rb cells ($1 \times 10^4$ cells/well) were incubated with AdV-luc (200 vp/cell) and control, freshly diluted vitreous, low molecular weight hyaluron, vitreous combined with low molecular weight hyaluron, at 100 micrograms Hyaluron per 100 microliters for 18 hours. Cells were harvested and assayed for luciferase activity.

The small insert of FIG. 12. displays the same data as the larger graph, but on a scale allowing the visualization of the enhancement effect generated by vitreous alone and the inhibitory effect generated by low molecular weight hyaluron alone. All were significantly different from control levels of expression.

Fresh Human conjunctival explants were incubated in 100 μl serum-free medium containing as indicated 0.5% vitreous or 100 μg hyaluron that had been digested with 10 units lyase for 1 hour. Cultures were examined under a confocal microscope after 24, 48 and 72 hours.

EXAMPLE 10

Figure 13:
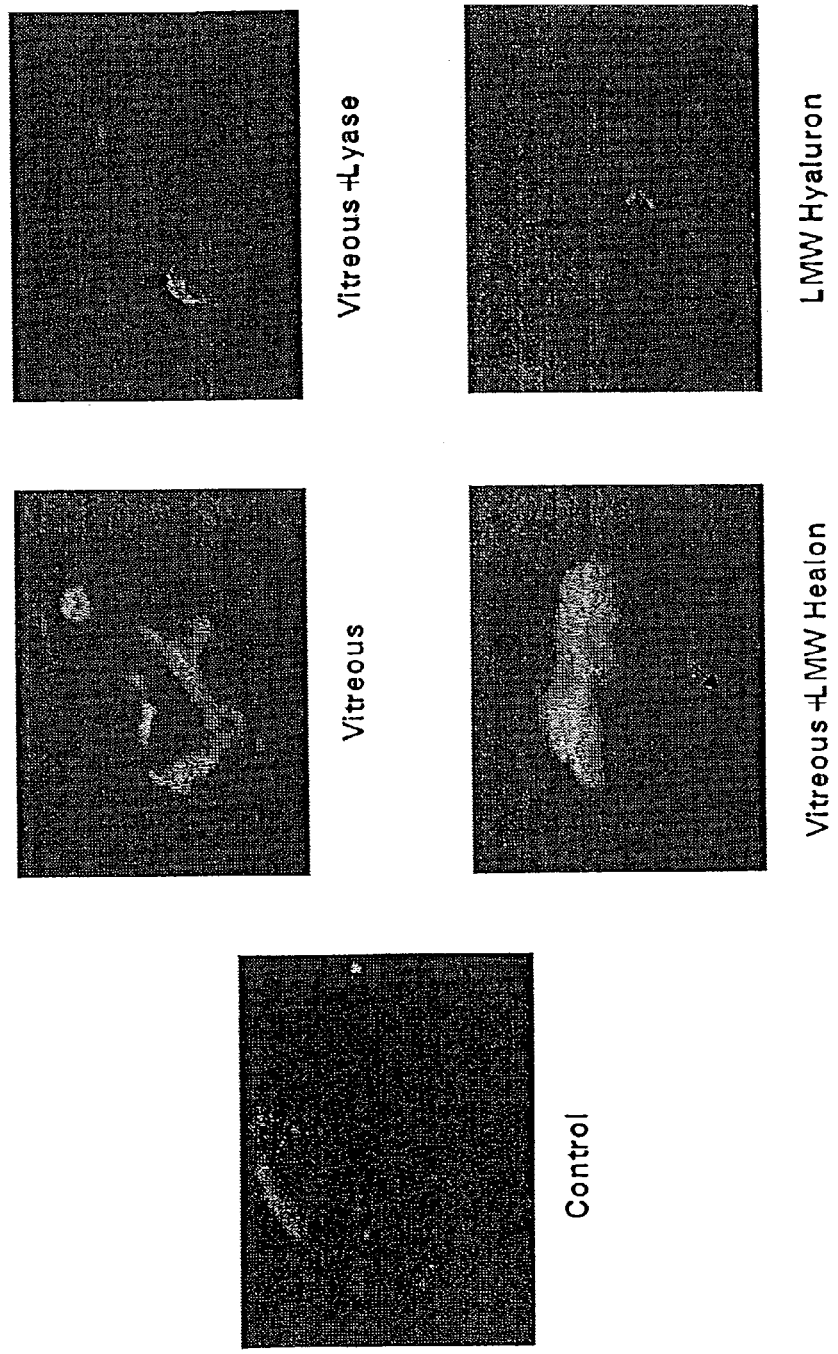
FIG. 13. Effect of Vitreous on Adenoviral mediated gene expression in human conjunctival explants.
Figure 15:
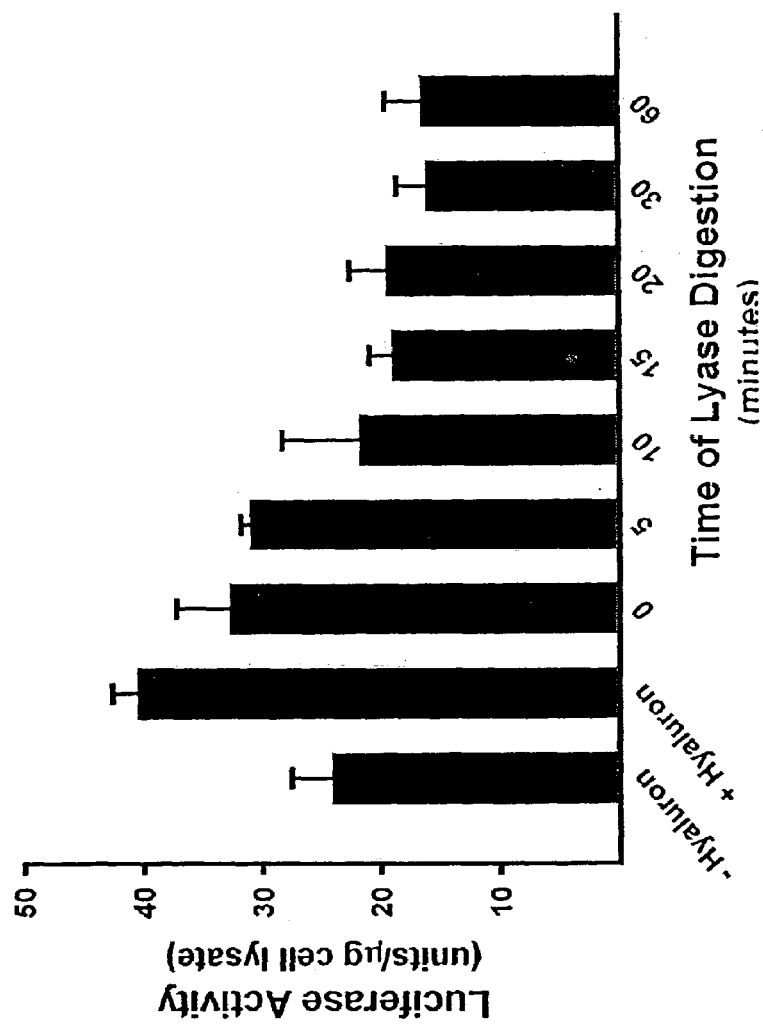
FIG. 15. Effect of Lyase-digested hyaluron on Adenoviral-mediated transgene expression.

Vitreous is Effective in Enhancing Expression, and Low Molecular Weight Hyaluron is Effective in Inhibiting Adenoviral Mediated Transgene Expression in Human Conjunctival Explants FIG. 13 shows the enhancement of adenoviral-mediated transgene expression in human conjunctival explants by incubation of the conjunctival tissue with vitreous. Also shown is the inhibition of adenoviral-mediated transgene expression by low molecular weight hyaluron. The effects of vitreous are abrogated by the treatment of vitreous with lyase. Similarly to the results in Example 9, the combination of vitreous and low molecular weight hyaluron resulted in many fold enhancement of transgene expression.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,141,973
U.S. Pat. No. 4,801,619
U.S. Pat. No. 4,808,526
U.S. Pat. No. 4,840,941
U.S. Pat. No. 5,670,488
U.S. Pat. No. 5,824,544
U.S. Pat. No. 5,932,210
U.S. Pat. No. 6,194,392
U.S. Pat. No. 6,218,373
U.S. Pat. No. 6,258,791
U.S. Pat. No. 6,271,216
Abe et al., *Proc. Soc. Exp. Biol. Med.*, 203:354–359, 1993.
Arap et al., *Cancer Res.*, 55(6):1351–1354, 1995.
Banerjee et al. *Cancer Res.*, 52:6297–6304, 1992.
Batra et al., *Am. J Respir. Cell Mol. Biol.*, 21(2):238–45, 1999.
Behbakht et al., *Am. J. Obstet. Gynecol.*, 175(5):1260–1265, 1996.
Bett et al., *J. Virol.*, 67(10):5911–5921, 1993.
Blackwell et al., *Arch. Otolaryngol. Head. Neck Surg.*, 125(8):856–863, 1999.
Bussemakers et al., *Biochem. Biophys. Res. Commun.*, 182(1):318–324, 1992.
Caldas et al., *Nat. Genet.*, 8(1):27–32, 1994.
Casey et al. *Oncogene*, 6(10):1791–1797, 1991.
Chen et al., *Proc. Natl. Acad. Sci. USA*, 91(8):3054–7, 1994.
Chen et al., *Proc. Natl. Acad. Sci. USA*, 92(7):2577–2581, 1995.
Cheng et al., *Cancer Res.*, 54(21):5547–5551, 1994.
Cheung et al., *J. Biol. Chem.*, 268(32):24303–24310, 1993.
Chillon et al., *J. Virol.*, 73(3):2537–40, 1999.
Chroboczek et al., *Virology*, 186:280–285, 1992.
Dorai et al., *Int. J. Cancer*, 82(6):846–52, 1999.
Eastham et al., *Hum. Gene Ther.*, 7(4):515–23, 1996.
Edelman and Crossin, *Annu. Rev. Biochem.*, 60:155–90, 1991.
Edelman, *Ann. Rev. Biochem.*, 54:135–169, 1985.
Esandi et al., *Gene Ther.*, 4(4):280–7, 1997.
Evans, *Am. J. Hyg.* 67:256–263, 1958.
Feldman et al., *Cardiovasc. Res.*, 32(2):194–207, 1996.
Flomenberg et al., *J. Infect. Dis.*, 169:775–781, 1994.
Frixen et al., *J. Cell. Biol.*, 113(1):173–185, 1991.
Giancotti and Ruoslahti, *Cell* 60(5):849–859, 1990.
Goebel et al., *Ann. Otol. Rhinol. Laryngol.*, 105(7):562–7, 1996.
Golasten et al, *New Engl. J. Med.*, 309(11983):288–296, 1983.
Gonzalez-Zulueta et al., *Cancer Res.*, 55(20):4531–4535, 1995.
Graham and Prevec, *Mol Biotechnol.*, 3(3):207–20, 1995.
Han et al., *Biol. Pharm. Bull.*, 22(8):836–40, 1999.
Herman et al., *Cancer Res*, 55(20):4525–30, 1995.
Hermens and Verhaagen, *Prog. Neurobiol.*, 55(4):399–432, 1998.
Hoekstra, In: *Hyaluronan-modified surfaces for medical devices*, Medical Device and Diagnostic Industry Magazine, 1999.
Hollstein et al., *Science*, 253:49–53, 1991.
Horwitz, In: *Virology*, 2d edit., Fields (Ed.), Raven Press, Ltd. New York, 1990.
Hurwitz et al., *Hum. Gene Ther.*, 10:441–48, 1999.
Hussussian et al., *Nat. Genet.*, 8(1):15–21, 1994.
Irie et al., *Antisense Nucleic Acid Drug Dev.*, 9(4):341–9, 1999.
Ishibashi et al, *J. Clin. Invest.*, 92:883–893, 1993.
Ishibashi et al, *J. Clin. Invest.*, 93:1885–1893, 1994.

Jiang et al., *Proc. Nat'l Acad. Sci. USA*, 93:9160–9165, 1996.
Kamb et al., *Nat.Genet.*, 8(1):23–2, 1994.
Klaassen, In: *The Pharmacological Basis of Therapeutics*, Goodman and Gilman, Eds., Pergamon Press, 8th Ed., pp. 49–61, 1990.
Kreil, *Protein Sci.*, 4(9):1666–9, 1995.
Lee and Spicer, *Curr. Opin. Cell Biol.*, 12, 581–586, 2000.
Lesch, *Biol. Psychiatry*, 45(3):247–53, 1999.
Lin and Guidotti, *J. Biol. Chem.*, 264:14408–14414, 1989.
Marienfeld et al., *Gene Ther.*, 6(6):1101–13, 1999.
Matsura et al., *Biochim. Biophys. Acta*, 1123(3):309–315, 1992.
Merlo et al., *Nat. Med.*, 1(7):686–692, 1995.
Mincheff et al., *Eur. Urol.*, 38(2):208–17, 2000.
Mori et al., *Cancer Res.*, 54(13):3396–3397, 1994.
Morrison et al., *J. Gen. Virol.*, 78(Pt 4):873–8, 1997.
Neumann et al., *Virus Res.*, 7:93–97, 1987.
Nobori et al., *Nature*, 368(6473):753–756, 1994.
O'Malley et al., *Cancer Res.*, 55(5): 1080–5, 1995.
Obrink, *Bioessays*, 13(5):227–234, 1991.
Odin and Obrink, *Exp. Cell Res.*, 171(1):1–15, 1987.
Okamoto et al., *Proc. Natl. Acad. Sci. USA*, 1(23):11045–11049, 1994.
Orlow et al., *Cancer Res*, 54(11):2848–2851, 1994.
Parks et al., *J. Virol.*, 71(4):3293–8, 1997.
Petrof, *Eur. Respir. J.*, 11 (2):492–7, 1998.
Reddy et al., *Virology*, 251(2):414–26, 1998.
Remington's Pharmaceutical Sciences, 18th Ed. Mack Printing Company, pp. 1289–1329, 1990.
Robbins et al., *Trends Biotechnol.*, 16(1):35–40, 1998.
Rooney et al., *Lancet.*, 345:9–12, 1995.
Rosenfeld et al., *J. Mol. Med.*, 74(8):455–62, 1996.
Sambrook, In: *Molecular Cloning*, Cold Spring Harbor Laboratory Press, 2001.
Schmitz et al., *Am. J. Epidemiol.*, 117:455–466, 1983.
Serrano et al., *Nature*, 366:704–707, 1993.
Serrano et al., *Science*, 267(5195):249–252, 1995.
SIGMA™ 2002–2003 Catalog of Biochemical and Reagents for Life Science research. Sigma-Aldrich Co., Inc. P.O. Box 14508, St. Louis, Mo. 63178, USA, 2002
Spandidos et al., *Anticancer Res.*, 10:1543–1554, 1990.
Spicer and McDonald, *J. Biol. Chem.*, 273:1923–1932, 1998
Spicer, *Methods Mol. Biol.*,171:73–382, 2001.
Stewart et al., *Gene Ther.*, 6(3):350–63, 1999.
Su et al., *Cancer Res.*, 58, 2339–2342, 1998.
Takahasi and Sawasaki, *In Vitro Cell Dev. Biol.*, 28A(6): 380–382, 1992.
Tanzawa et al, *FEBS Letters*, 118(1):81–84, 1980.
Umbas et al., *Cancer Res.*, 52(18):5104–5109, 1992.
Vanderkwaak and Alvarez, *Curr. Opin. Obstet. Gynecol.*, 11(1):29–34, 1999.
Wadell et al, *Ann. NY Acad. Sci.*, 354:16–42, 1980.
Watanabe, *Atherosclerosis*, 36:261–268, 1986.
Weinberg, *Science*, 254(5035): 1138–1146, 1991.
Wilson, *J. Clin. Invest.*, 98(11):2435, 1996.
Wilson, *Nature*, 365:691–692, 1993.
Yotnda et al., *Gene Ther.*, 8:930–37, 2001.
Zheng et al., *J. Gen. Virol.*, 80(Pt 7):1735–42, 1999.

We claim:

1. A method of gene delivery to cells of the eye in a subject for treating a cancer of the eye in a subject comprising administering to the eye of said subject an AdV5/F35 vector comprising a transgene that encodes a therapeutic protein, wherein expression of said therapeutic protein results in treatment of cancer of the eye.

2. The method of claim 1, wherein said subject is human.

3. The method of claim 2, wherein said vector is administered into the eye.

4. The method of claim 3, wherein said vector is administered via intravitreous injection.

5. The method of claim 1, wherein said cancer is retinoblastoma.

6. The method of claim 1, wherein said method of gene delivery is combined with administration of a second therapeutic agent.

7. The method of claim 6, wherein said transgene is thymidine kinase.

8. The method of claim 7, wherein said thymidine kinase is herpes simplex virus thymidine kinase.

9. The method of claim 7, wherein said second therapeutic agent is ganciclovir.

10. The method of claim 9, wherein ganciclovir is administered intravenously.

11. The method of claim 10, wherein the number of tumors in said subject is reduced.

12. The method of claim 1, wherein said transgene is p53 or a retinoblastoma gene.

* * * * *